United States Patent [19]

Watanabe et al.

[11] Patent Number: 5,578,596
[45] Date of Patent: Nov. 26, 1996

[54] 2-ALKOXY-5,6,7,8-TETRAHYDROQUINOX-ALINE DERIVATIVES, AND PRODUCTION METHOD AND USE THEREOF

[75] Inventors: Hideyuki Watanabe; Masao Yaso; Daisuke Mochizuki, all of Shizuoka, Japan

[73] Assignee: Asahi Kasei Kogyo Kabushiki Kaisha, Osaka, Japan

[21] Appl. No.: 432,168

[22] PCT Filed: Nov. 4, 1993

[86] PCT No.: PCT/JP93/01589

§ 371 Date: May 8, 1995

§ 102(e) Date: May 8, 1995

[87] PCT Pub. No.: WO94/11362

PCT Pub. Date: May 25, 1994

[30] Foreign Application Priority Data

Nov. 9, 1992 [JP] Japan .................... 4-298996

[51] Int. Cl.$^6$ .................... A61K 31/495; A61K 31/505; C07D 401/12; C07D 403/12
[52] U.S. Cl. .................... 514/249; 544/295; 544/354
[58] Field of Search .................... 544/354, 295; 514/249

[56] References Cited

U.S. PATENT DOCUMENTS

| | | | |
|---|---|---|---|
| 4,894,453 | 1/1990 | Yaso et al. | 544/354 |
| 5,001,237 | 3/1991 | Yaso et al. | 540/575 |

FOREIGN PATENT DOCUMENTS 63-107968  5/1988  Japan .

OTHER PUBLICATIONS

Matsuki et al., Jpn. J. Pharmacol. Suppl., 58, 313 (1992), p. 313.
Saxena et al., TiPs (Mar. 1990) vol. 11, pp. 95–96.
Feighner et al. (1989), *Psychopathology 1989;* 22(supp); 21–26.
Hisayama et al. Jap. J. Clin. Med., vol. 46 (Sp.Ed.) (1989) pp. 1241–1248 w/translation (partial).

*Primary Examiner*—Emily Bernhardt
*Attorney, Agent, or Firm*—Birch, Stewart, Kolasch & Birch, LLP

[57] ABSTRACT

Disclosed are a compound represented by formula (1) and a non-toxic salt thereof, a production method thereof, and a pharmaceutical composition for treating a serotonergic neuron-related disease comprising the same as an active ingredient:

$$\text{structure} \quad (1)$$

wherein $R^1$ represents a hydrogen atom or a lower alkyl group; $R^2$ represents a pyridyl group which is unsubstituted or substituted with 1 to 3 substituents each independently selected from the group consisting of a halogen atom, a lower alkyl group, a trifluoromethyl group, a lower alkoxy group, a carbamoyl group and a cyano group, or a pyrimidinyl group which is unsubstituted or substituted with 1 to 2 substituents each independently selected from the group consisting of a lower alkyl group and a lower alkoxy group; and n is an integer of from 2 to 5. Compound (1) of the present invention and a non-toxic salt thereof have a strong affinity for serotonin 1A receptor and, therefore, they are useful for preventing and treating serotonergic neuron-related diseases, such as motion sickness, space sickness, emesis, dizziness, depression, anxiety, eating disorder, and the like.

3 Claims, No Drawings

2-ALKOXY-5,6,7,8-TETRAHYDROQUINOXALINE DERIVATIVES, AND PRODUCTION METHOD AND USE THEREOF

This application is a 371 of PCT/JP93/01589 filed Nov. 4, 1993.

1. Technical Field

The present invention relates to novel 2-alkoxy-5,6,7,8-tetrahydroquinoxaline derivatives, a production method thereof, and a pharmaceutical use thereof. The 2-alkoxy-5,6,7,8-tetrahydroquinoxaline derivatives are useful for preventing and treating motion sickness, space sickness, emesis, dizziness, depression, anxiety, eating disorder, and the like.

2. Background Art

It has been known that compounds having an affinity for a serotonin 1A receptor are useful for preventing and treating motion sickness, space sickness, emesis, dizziness, depression, anxiety, eating disorder, and the like. With respect to such compounds, a number of studies have been made and the results thereof have been reported [see, "Nippon Rinsho (Japanese Journal of Clinical Medicine)" vol. 47, special edition, pp. 1241–1248 (1989); J.P. Feighnev, W.F. Boyer, Psychopathology, 22, 21 (1989); P.R. Saxena, C.M. Villalon, TiPS, 11, 95 (1990); N. Matsuki, et al., Jpn. J. Pharmacol. Suppl., 58, 313 (1992); etc.]. On the other hand, Unexamined Japanese Patent Application Laid-open Specification No. 63-107968 discloses 2-[2-(4-substituted phenyl-1-piperazinyl)ethoxy]-5,6,7,8-tetrahydroquinoxaline derivatives which have platelet agglutination suppressive, vasodilative and lipoperoxide formation suppressive activities. In this prior art document, however, there is no description with respect to the usefulness of such derivatives for preventing and treating serotonergic neuron-related diseases.

Problems to be Solved by the Invention

It has been desired in the art to develop and provide a compound which exhibits excellent pharmacological activities against serotonergic neuron-related diseases.

Means for Solving the Problems

In order to solve the above-mentioned problems accompanying the prior art compounds or derivatives, the present inventors have synthesized various types of compounds and have examined the compounds with respect to the pharmacological properties thereof. As a result, it has unexpectedly been found that 2-alkoxy-5,6,7,8-tetrahydroquinoxaline derivatives represented by formula (1) below, which have never been reported in any of the literature, exhibit an excellent affinity for a serotonin 1A receptor and excellent pharmacological activities against serotonergic neuron-related diseases. The present invention has been completed, based on the above novel findings.

Accordingly, it is an object of the present invention to provide a novel compound represented by formula (1) or a non-toxic salt thereof

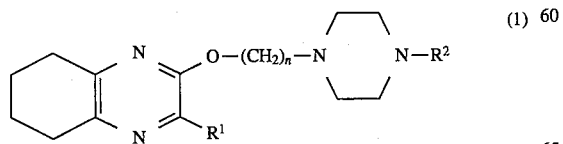

wherein $R^1$ represents a hydrogen atom or a lower alkyl group; $R^2$ represents a pyridyl group which is unsubstituted or substituted with 1 to 3 substituents each independently selected from the group consisting of a halogen atom, a lower alkyl group, a tri-fluromethyl group, a lower alkoxy group, a carbamoyl group and a cyano group, or a pyrimidinyl group which is unsubstituted or substituted with 1 to 2 substituents each independently selected from the group consisting of a lower alkyl group and a lower alkoxy group; and n is an integer of from 2 to 5.

It is another object of the present invention to provide a method for producing the above-mentioned novel compound represented by formula (1) or a non-toxic salt thereof, which comprises reacting, in an inert solvent, a compound represented by formula (2):

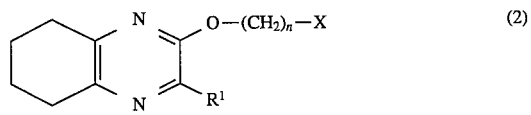

wherein $R^1$ and n are as defined for formula (1) above; and X represents a reactive leaving group, with a compound represented by formula (3):

wherein $R^2$ is as defined for formula (1) above.

It is a further object of the present invention to provide a pharmaceutical composition for treating a serotonergic neuron-related disease, which comprises, as an active ingredient, the above-mentioned novel compound represented by formula (1) or a non-toxic salt thereof.

The compound represented by formula (1) of the present invention (which compound is hereinafter, frequently referred to as "compound (1)") can be produced, for example, by reacting, in an inert solvent, a compound represented by formula (2) (which compound is hereinafter, frequently referred to as "compound (2)") with a compound represented by formula (3) (which compound is hereinafter, frequently referred to as "compound (3)").

In formula (2), the lower alkyl group defined by $R^1$ means a straight chain or branched $C_1$–$C_6$ alkyl group. Examples of lower alkyl groups include methyl, ethyl, propyl, isopropyl, butyl, isobutyl, sec-butyl, pentyl, hexyl, and the like.

The group represented by "X" in formula (2) is a reactive leaving group. In the present specification, the term "reactive leaving group" means a group which can enhance the reactivity of compound (2) to compound (3) and is adapted to leave compound (2) upon reaction of compound (2) with compound (3). Examples of reactive leaving groups include a halogen atom, such as a fluorine atom, a chlorine atom, a bromine atom and an iodine atom, and an alkyl- or aryl-sulfonyloxy group, such as methanesulfonyloxy, benzenesulfonyloxy and p-toluenesulfonyloxy.

Compound (2) is a novel compound, which has not been reported in any of the literature. Compound (2) can be produced, for example, by the following sequence of steps:

(a) reacting a compound represented by formula (4) (hereinafter, frequently referred to as "compound (4)"):

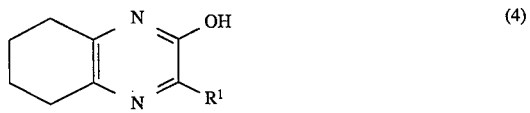

wherein $R^1$ is as defined for formula (1) above with an alkali metal alkoxide (e.g., sodium methoxide) in an alcohol solvent (e.g., methanol), followed by distilling-off the alcohol solvent in vacuo from the resultant reaction mixture, or reacting compound (4) with an alkali metal hydride (e.g., sodium hydride or potassium hydride) in an organic solvent (e.g., tetrahydrofuran), thereby obtaining an intermediate compound represented by formula (5) (hereinafter, frequently referred to as "compound (5)"):

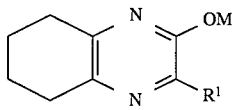  (5)

wherein $R^1$ is as defined for formula (1) above; and M is an alkali metal atom, such as sodium or potassium;

(b) reacting compound (5) with a compound represented by formula (6) (hereinafter, frequently referred to as "compound (6)"):

$$Y-(CH_2)_{n-1}-COOR^3 \quad (6)$$

wherein Y represents a halogen atom; $R^3$ represents a lower alkyl group; and n is as defined for formula (1) above in an inert solvent, thereby obtaining an intermediate compound represented by formula (7) (hereinafter, frequently referred to as "compound (7)"):

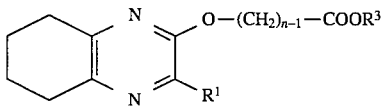  (7)

wherein $R^1$, $R^3$ and n are as defined for formulae (1) and (6) above;

(c) reacting compound (7) with a reducing agent in an inert solvent, thereby obtaining an intermediate compound represented by formula (8) (hereinafter, frequently referred to as "compound (8)"):

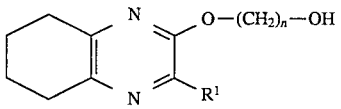  (8)

wherein $R^1$ and n are as defined for formula (1) above; and (d) reacting compound (8) with a halogenating agent (e.g., thionyl chloride) or a sulfonating agent (e.g., methanesulfonyl chloride) in an inert solvent, to thereby convert the hydroxyl group in compound (8) into a reactive leaving group (X), thus, obtaining compound (2).

Compound (2) can also be produced via another route, in which the above-mentioned compound (4) is reacted, in an inert solvent, with a compound represented by formula (9) (hereinafter, frequently referred to as "compound (9)"):

$$Y-(CH_2)_n-Z \quad (9)$$

wherein Z represents a halogen atom; and n and Y are as defined for formulae (1) and (6) above, respectively.

Compounds (7) and (8) above are also novel compounds, which have never been reported in any of the literature.

Compound (4), which is used in the above-mentioned reaction, is a known compound and is described in Unexamined Japanese Patent Application Laid-open Specification No. 63-107968 and can be synthesized according to the process described therein. Compounds (6) and (9) are also known compounds and listed in reagent catalogs as commercially available products.

In the reaction for obtaining compound (5) from compound (4), as the alkali metal reagent (alkali metal alkoxide or alkali metal hydride), there can be employed ployed an alkali metal alkoxide, such as lithium methoxide, sodium methoxide, potassium methoxide, sodium ethoxide, potassium ethoxide or potassium t-butoxide, or an alkali metal hydride, such as lithium hydride, sodium hydride or potassium hydride.

The alkali metal reagent may be used in an equivalent amount to that of compound (4). However, the alkali metal reagent is usually used in slight excess relative to the amount of compound (4).

As the solvent to be used in the reaction for obtaining compound (5) from compound (4), an alcohol, such as methanol, ethanol, propanol, butanol or t-butanol, can be employed.

The above-mentioned reaction for obtaining compound (5) can be conducted at a temperature within the range of from −10° C. to room temperature, and usually within the range of from −5° C. to 0° C. The reaction can be completed within 10 minutes to 1 hour. The amount of the solvent may be suitably selected. For example, the solvent is used in an amount which is 5 to 100 times the volume amount of compound (4).

Then, compound (5) obtained in the above step is reacted with compound (6) to thereby obtain compound (7). Examples of compound (6) include methyl and ethyl esters of bromoacetic acid, methyl and ethyl esters of chloroacetic acid, methyl and ethyl esters of 3-bromo-propionic acid, methyl and ethyl esters of 3-chloropropionic acid, methyl and ethyl esters of 4-bromobutyric acid, methyl and ethyl esters of 4-chlorobutyric acid, methyl and ethyl esters of 5-bromovaleric acid, methyl and ethyl esters of 5-chlorovaleric acid, and the like.

With respect to the inert solvent to be used in the reaction of compound (5) with compound (6), there is no specific limitation as long as the solvent does not have an adverse influence on the reaction. As examples of inert solvents, benzene, toluene, xylene, dimethylformamide, acetonitrile, acetone and t-butyl alcohol can be mentioned. The amount of the inert solvent may be suitably selected. For example, the inert solvent is used in a volume amount which is 10 to 200 times the volume amount of compound (6). In the reaction, compound (6) may be used in an equivalent amount to that of compound (5). However, compound (6) is usually used in slight excess relative to the amount of compound (5).

The above-mentioned reaction of compound (5) with compound (6) may be conducted at room temperature or under heating. For example, the reaction is conducted at a temperature within the range of from 50° to 120° C. The reaction time may be suitably selected, depending on the types of compounds (5) and (6) and the reaction temperature. The reaction can be terminated upon confirming that a sufficient degree of reaction for the production of compound (7) has been achieved. The reaction is usually completed within 1 hour to 1 day.

Then, compound (7) obtained in the above step is reacted with a reducing agent, to thereby obtain compound pound (8). Examples of reducing agents include an alkali metal hydride, such as lithium aluminum hydride. The reducing agent may be used in an equivalent amount to that of compound (7). However, the reducing agent is usually used in an amount within the range of from 1 to 5 equivalents, preferably 1 to 2 equivalents per equivalent of compound (7).

With respect to the inert solvent to be used in the above-mentioned reducing reaction of compound (7), there is no specific limitation as long as the solvent does not have an adverse influence on the reaction. Examples of inert solvents include tetrahydrofuran and 1,4-dioxane. The amount of the inert solvent may be suitably selected. For example, the inert solvent is used in a volume amount which is 10 to 200 times the volume amount of compound (7).

The above-mentioned reducing reaction of compound (7) may be conducted at a temperature within the range of from −20° C. to room temperature. For example, the reaction is conducted at a temperature within the range of from −10° to 10° C. The reaction time may be suitably selected, depending on the reaction temperature and the like. The reaction can be terminated upon confirming that a sufficient degree of reaction for the production of compound (8) has been achieved. The reaction is usually completed within 1 hour to 1 day.

Then, compound (8) obtained in the above step is converted into compound (2), in which the hydroxyl group of compound (8) is substituted with a halogen atom or an alkyl- or arylsulfonyloxy group. This conversion reaction may be conducted in a conventional manner. For example, for the conversion of the hydroxyl group of compound (8) into a halogen atom, compound (8) is reacted with a halogenating agent such as thionyl chloride or phosphorus pentachloride.

On the other hand, for the conversion of the hydroxyl group of compound (8) into an alkyl- or aryl-sulfonyloxy group (e.g., methanesulfonyloxy, benzene-sulfonyloxy or p-toluenesulfonyloxy), compound (8) is reacted with a sulfonating agent, such as an alkyl- or arylsulfonyl chloride (e.g., methanesulfonyl chloride or p-toluenesulfonyl chloride) which corresponds to the desired alkyl- or arylsulfonyloxy group.

The above-mentioned conversion reaction of compound (8) to compound (2) can be conducted in an inert solvent, such as methylene chloride or chloroform. The halogenating agent can be used in an amount within the range of from about 1.0 to 1.2 equivalents per equivalent of compound (8). The conversion reaction can be conducted at room temperature or below (for example, under ice-cooling) for 1 hour to 1 day. The amount of the solvent may be suitably selected. However, it is preferred to use the solvent in a volume amount which is 5 to 100 times the volume amount of compound (8).

As mentioned above, compound (2) can also be produced by reacting compound (4) with compound (9). Examples of compounds (9) include an alkane dihalide, such as 1,2-dibromoethane, 1,2-dichloroethane, 1-bromo-2-chloroethane, 1,3-dibromopropane, 1,3-dichloropropane, 1-bromo-3-chloropropane, 1,4-dibromobutane, 1,4-dichlorobutane, 1-bromo-4-chlorobutane, 1,5-dibromopentane, 1,5-dichloropentane, 1-bromo-5-chloropentane, and the like.

With respect to the inert solvent to be used in the reaction of compound (4) with compound (9), there is no specific limitation as long as it does not have an adverse influence on the reaction. Preferred examples of inert solvents include benzene, toluene, xylene, dimethylformamide, acetonitrile, acetone and the like. The amount of the inert solvent may be suitably selected. For example, the inert solvent is used in a volume amount which is 10 to 200 times the volume amount of compound (4).

It is preferred to conduct the reaction of compound (4) with compound (9) in the presence of a deacidifying agent. The deacidifying agent to be used can be an inorganic or an organic base. Examples of deacidifying agents include carbonates, bicarbonates and hydrides of alkali metals, such as potassium carbonate, sodium carbonate, Sodium bicarbonate and sodium hydride; tertiary amines, such as triethylamine, pyridine and 1,8-diazabicyclo[5.4.0]undeca-7-ene (DBU); and the like.

In the above-mentioned reaction of compound (4) with compound (9), a reaction promoter, such as sodium iodide or potassium iodide, may be added to the reaction system.

Compound (9) may be used in an equivalent amount to that of compound (4). However, compound (9) is usually used in an amount within the range of from 1 to 5 equivalents, preferably 1.2 to 2.0 equivalents per equivalent of compound (4). With respect to the deacidifying agent, the amount to be employed is usually 1 to 2 equivalents per equivalent of compound (9).

The reaction of compound (4) with compound (9) can proceed at room temperature. However, it is preferred to conduct the reaction by heating, advantageously under reflux of the solvent. The reaction time may be suitably selected, depending on the types of compounds (4) and (9) and the reaction temperature. The reaction can be terminated upon confirming that a sufficient degree of reaction for the production of compound (2) has been achieved. The reaction is usually completed within 1 hour to several days.

Compound (2) thus obtained is reacted with compound (3), to thereby obtain the desired compound represented by formula (1) of the present invention. Compound (3) to be used in the reaction is a compound represented by formula (3) above, wherein $R^2$ represents a pyridyl group which is unsubstituted or substituted with 1 to 3 substituents each independently selected from the group consisting of a halogen atom, a lower alkyl group, a trifluoromethyl group, a lower alkoxy group, a carbamoyl group and a cyano group, or a pyrimidinyl group which is unsubstituted or substituted with 1 to 2 substituents each independently selected from the group consisting of a lower alkyl group and a lower alkoxy group. Examples of halogen atoms include a fluorine atom, a chlorine atom, a bromine atom and an iodine atom. The lower alkyl group means a straight chain or branched $C_1$–$C_4$ alkyl group, such as methyl, ethyl, propyl, isopropyl or butyl group. The lower alkoxy group means a straight chain or branched $C_1$–$C_4$ alkoxy group, such as methoxy, ethoxy, propoxy, isopropoxy or butoxy group.

Compounds (3) are conventionally known compounds, and most of compounds (3) are commercially available. Alternatively, compounds (3) may be synthesized in a conventional manner.

With respect to the inert solvent to be used in the reaction of compound (2) with compound (3), there is no specific limitation as long as it does not have an adverse influence on the reaction. Preferred examples of inert solvents include benzene, toluene, xylene, dimethylformamide, acetonitrile, acetone and the like. The amount of the inert solvent may be suitably selected. For example, the inert solvent is used in a volume amount which is 10 to 200 times the volume amount of compound (2).

It is preferred to conduct the reaction of compound (2) with compound (3) in the presence of a deacidifying agent. The deacidifying agent to be used is an inorganic or organic base. Examples of deacidifying agents include carbonates, bicarbonates and hydrides of alkali metals, such as potassium carbonate, sodium carbonate, sodium bicarbonate and sodium hydride; tertiary amines, such as triethylamine, pyridine and 1,8-diazabicyclo[5.4.0]undeca-7-ene (DBU); and the like. Compound (3) may be used in an equivalent amount to that of compound (2). However, compound (3) is usually used in an amount within the range of from 1 to 5 equivalents, preferably 1.2 to 2.0 equivalents per equivalent of compound (2). With respect to the deacidifying agent, the amount to be employed is usually 1 to 2 equivalents per equivalent of compound (3).

The reaction of compound (2) with compound (3) for obtaining compound (1) can proceed at room temperature. However, it is preferred to conduct the reaction by heating, advantageously under reflux of the solvent. The reaction time may be suitably selected, depending on the types of compounds (2) and (3) and the reaction temperature. The reaction can be terminated upon confirming that a sufficient degree of reaction for the production of compound (1) has been achieved, wherein the confirmation is done by thin layer chromatography or high performance liquid chromatography. The reaction is usually completed within 1 hour to several days.

Isolation and purification of compound (1) from the reaction mixture of compound (2) with compound (3) can be performed by filtrating off the insoluble substances from the reaction mixture, concentrating the filtrate, and subjecting the resultant residue to column chromatography using silica gel or the like.

In producing intermediates including precursors of compound (2) as well as compound (2) during the process for the production of the desired compound (1) of the present invention, the reaction mixtures respectively containing the intermediates may be used in situ. Alternatively, compound (2) and the precursors thereof may be isolated and purified from the respective reaction mixtures. In this case, the purification of these compounds can be conducted by known methods, such as column chromatography, using silica gel or the like as a solid phase.

Specific examples of the thus obtained compounds (1) of the present invention are enumerated in Table 1.

TABLE 1

Py: pyridyl   Pm: pyrimidinyl
each of the numbers shown in parentheses indicates the position of substitution with $R^2$ in pyridyl or pyrimidinyl.

| Compound No. | $R^1$ | n | $R^2$ |
|---|---|---|---|
| 300 | H | 4 | -2-Py |
| 301 | H | 4 | -2-Pm |
| 409 | $CH_3$ | 4 | -2-Py |
| 410 | $CH_3$ | 4 | -2-Pm |
| 423 | $C_3H_7$ | 4 | -2-Py |
| 414 | $C_3H_7$ | 4 | -2-Pm |
| 431 | iso-$C_3H_7$ | 4 | -2-Py |
| 432 | iso-$C_3H_7$ | 4 | -2-Pm |
| 425 | $C_5H_{11}$ | 4 | -2-Py |
| 428 | $C_5H_{11}$ | 4 | -2-Pm |
| 517 | H | 2 | -2-Py |
| 521 | H | 2 | -2-Pm |
| 537 | H | 3 | -2-Py |
| 538 | H | 3 | -2-Pm |
| 511 | H | 5 | -2-Py |
| 512 | H | 5 | -2-Pm |
| 501 | H | 4 | -2-Py—$CH_3$(6) |
| 502 | H | 4 | -2-Py—Cl(3) |
| 557 | H | 4 | -2-Py—$OCH_3$(3) |
| 514 | H | 4 | -2-Py—CN(3) |
| 598 | H | 4 | -2-Py—$(CH_3)_2$(3, 6) |
| 500 | H | 4 | -2-Py—$CH_3$(6) |
| 524 | H | 4 | -2-Py—Cl(6) |
| 526 | H | 4 | -2-Py—$CONH_2$(3) |
| 539 | H | 4 | -2-Py—$OCH_3$(6) |
| 561 | H | 4 | -2-Py—CN(3)—$(CH_3)_2$(4, 6) |

TABLE 1-continued

Py: pyridyl   Pm: pyrimidinyl
each of the numbers shown in parentheses indicates the position of substitution with $R^2$ in pyridyl or pyrimidinyl.

| Compound No. | $R^1$ | n | $R^2$ |
|---|---|---|---|
| 569 | H | 4 | -2-Py—$(CH_3)_2$(4, 6) |
| 621 | H | 4 | -2-Py—$CF_3$(3) |
| 629 | H | 4 | -2-Py—$OC_3H_7$(6) |
| 630 | H | 4 | -2-Py—O-iso-$C_3H_7$(6) |
| 639 | H | 4 | -2-Py—$CF_3$(4) |
| 640 | H | 4 | -2-Py—$CF_3$(6) |
| 481 | H | 4 | -2-Pm—$(CH_3)_2$(4, 6) |
| 504 | H | 4 | -2-Pm—$CH_3$(4) |
| 549 | H | 4 | -2-Pm—$(OCH_3)_2$(4, 6) |
| 562 | H | 4 | -2-Pm—$OCH_3$(4)—$CH_3$(6) |

Compound (1) can be provided in the form of a pharmaceutically acceptable non-toxic salt thereof, if desired. Examples of non-toxic salts include salts of inorganic acids, such as hydrochloric acid, sulfuric acid and phosphoric acid; and salts of organic acids, such as acetic acid, propionic acid, tartaric acid, citric acid, glycolic acid, gluconic acid, succinic acid, malic acid, glutamic acid, aspartic acid and methanesulfonic acid.

The above-mentioned non-toxic salts of compound (1) of the present invention can be produced using a known method for producing salts from free bases. For example, the hydrochloride of compound (1) can be prepared by adding a solution of hydrochloric acid/methanol to compound (1) in an amount of 1 equivalent or more per equivalent of compound (1) to form the hydrochloride of compound (1) as a precipitate, and then collecting the precipitate. In this instance, when the hydrochloride of compound (1) is hardly deposited as a precipitate, an appropriate organic solvent (e.g., diethyl ether) can be added thereto to deposit the hydrochloride as a precipitate.

Compound (1) and a non-toxic salt thereof thus prepared exhibit a strong affinity for a serotonin 1A receptor, as mentioned below. Furthermore, the results of animal experiments which are also mentioned below show that compound (1) and a non-toxic salt thereof are effective for treating serotonergic neuron-related diseases, such as motion sickness. Thus, it has been confirmed that compound (1) and non-toxic salts thereof according to the present invention are useful in pharmaceutical compositions for treating serotonergic neuron-related diseases. For preparation of such a pharmaceutical composition, compound (1) or a non-toxic salt thereof can be combined with a pharmaceutically acceptable carrier by a conventional method.

The pharmaceutical composition for treating a serotonergic neuron-related disease according to the present invention may be administered to a patient orally or parenterally. For parenteral administration, the pharmaceutical composition can be used, for example, as an injection composition, such as a composition for intravenous drip. The dose of the pharmaceutical composition is varied depending on various factors, such as the manner of administration, age, weight, condition of the patient, etc. However, the dose may generally be about 0.1 to about 200 mg/kg per day for an adult in terms of the amount of compound (1).

The pharmaceutical composition of the present invention can be administered to a patient in the form of a solution for injection, tablet, pill, powder, granule or capsule. For the preparation of such a pharmaceutical composition, various types of pharmaceutically acceptable carriers can be employed, depending on the form of the pharmaceutical composition. For example, when compound (1) of the present invention is formulated into a medicine for oral administration (such as a tablet, granule, capsule or the like), there can be employed excipients, such as starch, lactose, refined sugar, mannitol, carboxymethyl cellulose, corn starch and inorganic salts; binders, such as methylcellulose, sodium salt of carboxymethyl cellulose, hydroxypropyl cellulose, crystalline cellulose, ethylcellulose, polyvinyl pyrrolidone and macrogol; disintegrating agents, such as starch, hydroxypropyl starch, carboxymethyl cellulose, sodium carboxymethyl cellulose and hydroxypropyl cellulose; surfactants, such as sodium laurylsulfate, soybean lecithin, sucrose esters of fatty acids and polysorbate 80; lubricants, such as talc, wax, hydrated vegetable oils, sucrose esters of fatty acids, magnesium stearate and calcium stearate; fluidity promoting agent; sweetening and flavoring agents; and the like.

The pharmaceutical composition of the present invention can be administered in the form of an emulsion, syrup or elixir.

When compound (1) of the present invention is formulated into a medicine for parenteral administration, a diluent, such as distilled water for injection, physiological saline, an aqueous solution of glucose, a vegetable oil for injection, propylene glycol or polyethylene glycol, can be used. In addition, if desired, other additives, such as a germicide, antiseptic, stabilizer, isotonicity agent and soothing agent, can be used.

Effect of the Invention

In order to demonstrate the pharmacological activities of compound (1) and a non-toxic salt thereof of the present invention, tests were conducted with respect to compounds (1) synthesized in Examples described below. The procedures and results of the tests are as follows.

Each of the compounds (1) used in the following tests was represented by the number indicated in the corresponding Example, and was tested in the form of a hydrochloride salt thereof.

1. Affinity for serotonin 1A (5HT1A) receptor
(1) Method
(A) Preparation of rat hippocampal membrane fraction A male SD strain rat (7-week old; Charles River) was decapitated, and brain was taken out therefrom quickly. 50 mM Tris-HCl buffer (pH 7.4) was added to the brain under ice cooling to obtain a suspension. The resultant suspension was homogenized, and then subjected to centrifugation at 48000 g for 15 minutes, to thereby obtain a precipitate. The precipitate was resuspended in the same Tris-HCl buffer as used above. The resultant suspension was incubated at 30° C. for 20 minutes to decompose endogenous serotonin of the rat hippocampal membrane, followed by centrifugation at 48000 g for 15 minutes to thereby obtain a precipitate. The resultant precipitate was used as a rat hippocampal membrane fraction in the following procedures.

(B) Method for the evaluation of the binding ability of $^3$H-8-hydroxy-dipropylaminotetralin ($^3$H-8-OH-DPAT) to serotonin 1A receptor The rat hippocampal membrane fraction prepared in step (A) above (about 100 to 200 μg in terms of proteins) was reacted with 0.5 nM (final concentration) $^3$H-8-OH-DPAT (which is commercially available from DuPont-NEN Research Products) and 10 μM (final concentration) pargyline (which is commercially available from Sigma Chemical Company) at 30° C. for 30 minutes to effect a reaction.

The resultant reaction mixture was subjected to suction filtration using a Whatman GF/C filter, to thereby terminate the reaction. The radio-activity of $^3$H-8-OH-DPAT adsorbed on the filter was determined using a liquid scintillation counter. The obtained value is regarded as a total amount (TB) of specifically binding $^3$H-8-OH-DPAT and non-specifically binding $^3$H-8-OH-DPAT.

On the other hand, substantially the same procedure as mentioned above was repeated, except that 10 μM (final concentration) serotonin was added to the $^3$H-8-OH-DPAT and pargyline. The radioactivity of $^3$H-8-OH-DPAT adsorbed on the filter was determined in the same manner as mentioned above. The obtained value is regarded as the amount (NB) of non-specifically binding $^3$H-8-OH-DPAT.

Further, substantially the same procedure as mentioned above was repeated, except that, instead of serotonin, a test compound was used in a predetermined concentration. The radioactivity of $^3$H-8-OH-DPAT adsorbed on the filter was determined in the same manner as mentioned above. The obtained value is regarded as the amount (DTB) of binding $^3$H-8-OH-DPAT.

(C) Calculation of Ki value

The inhibition ratio of the test compound (at a certain concentration) against the binding of 3H-8-OH-DPAT (the inhibition ratio is hereinafter referred to simply as "binding inhibition ratio") was calculated according to the following formula:

$$\text{Binding inhibition ratio (\%)} = 100 - (DTB - NB) \div (TB - NB) \times 100$$

With respect to each of the test compounds, the binding inhibition ratios at various concentrations (from a higher concentration to a lower concentration) were determined. The binding inhibition ratios were plotted, taking the logarithmic value of the concentration of test compound as the abscissa value, and the binding inhibition ratio as the ordinate value. Then, a curve was drawn by non-linear least square method. From the curve thus drawn, the IC$_{50}$ value (the concentration at which a test compound inhibits the binding of $^3$H-8-OH-DPAT to the serotonin 1A receptor by 50%) was determined with respect to each of the test compounds.

The Ki value was determined according to the following formula:

$$Ki = IC_{50} \div (1 + [L]/Kd)$$

wherein:
[L] is the concentration (0.2 nM) of a radioactive ligand ($^3$H-8-OH-DPAT) used in the test;
Kd is the concentration (0.7174 nM) at which the radioactive ligand ($^3$H-8-OH-DPAT) exhibits the affinity for the serotonin 1A receptor; and
IC$_{50}$ is the concentration of a test compound at which the test compound inhibits the binding of the radioactive ligand ($^3$H-8-OH-DPAT) to the serotonin 1A receptor by 50%.

(2) Results

The Ki values of the individual test compounds to the serotonin 1A (5HT1A) receptor are shown in Table 2.

TABLE 2

| Test compound (hydrochloride) | 5HT 1A Ki (nM) |
| --- | --- |
| 300 | 1.6 |
| 301 | 6 |

TABLE 2-continued

| Test compound (hydrochloride) | 5HT 1A Ki (nM) |
| --- | --- |
| 409 | 16 |
| 410 | 24 |
| 537 | 14 |
| 538 | 25 |
| 511 | 8.4 |
| 512 | 23 |
| 501 | 0.6 |
| 502 | 13 |
| 557 | 1.5 |
| 514 | 4.8 |
| 598 | 25 |
| 500 | 2.1 |
| 524 | 1.9 |
| 539 | 1.3 |
| 561 | 16 |
| 569 | 6.8 |
| 629 | 1.8 |
| 630 | 3 |
| 639 | 11 |
| 640 | 5.2 |
| 481 | 5.3 |
| 504 | 3.9 |
| 549 | 6.6 |
| 562 | 11 |

2. Activities against motion sickness (1) Method

The activities of individual compounds against motion sickness were examined using Suncus murinus. Suncus murinus is a small animal belonging to the Soricidae family. It has been known that suncus is likely to suffer from motion sickness and is susceptible to occurrence of emesis [see "Seitai-no-kagaku (Science of living body)", 41, 538 (1990)]. Suncus is likely to show symptoms like the symptoms of human motion sickness under the stimulus of simple acceleration, finally leading to the occurrence of emesis. It has been recognized that motion sickness is caused by the occurrence of disorder in information, such as vision, equilibrium sense and the like, or by a stimulus which has never been memorized. Further, it has been recognized that the disorder in the inner earvestibular nucleus pathway and the high-order function of brain take part in the occurrence of motion sickness. Therefore, medicines capable of suppressing the occurrence of emesis of suncus would be useful for preventing and treating motion sickness, space sickness, emesis, dizziness and the like.

In this test, test compounds were individually administered intraperitoneally to suncus. 30 minutes after the administration, acceleration-stimulus (amplitude: 4 cm; frequency; 1 Hz) was given to the suncus, and the suncus thus treated was observed for 10 minutes as to whether emesis occurred or not.

(2) Results

The time for occurrence of emesis was measured with respect to each of the test compounds, and the results are shown in Table 3.

TABLE 3

| Test compound | Dose | Time for occurrence of emesis | Number of tested suncus |
| --- | --- | --- | --- |
| Physiological saline | | 1 min. 35 sec. ± 8 sec. | 46 |
| 300 (hydrochloride) | 1 mg/kg | Emesis did not occur | 4 |
| 301 (hydrochloride) | 3 mg/kg | Emesis did not occur | 4 |
| 501 (hydrochloride) | 1 mg/kg | Emesis did not occur | 4 |

TABLE 3-continued

| Test compound | Dose | Time for occurrence of emesis | Number of tested suncus |
| --- | --- | --- | --- |
| 500 (hydrochloride) | 1 mg/kg | Emesis did not occur | 4 |
| 524 (hydrochloride) | 1 mg/kg | Emesis did not occur | 4 |
| 539 (hydrochloride) | 1 mg/kg | Emesis did not occur | 4 |
| 629 (hydrochloride) | 3 mg/kg | Emesis did not occur | 4 |
| 630 (hydrochloride) | 3 mg/kg | Emesis did not occur | 4 |
| 504 (hydrochloride) | 1 mg/kg | Emesis did not occur | 4 |
| 562 (hydrochloride) | 3 mg/kg | Emesis did not occur | 4 |

As shown in Table 3, with respect to the suncuses to which physiological saline alone have been administered as a control, motion sickness was induced with respect to 100% of the suncuses, and emesis occurred within 2 minutes from the stimulation. By contrast, with respect to the suncuses to which the hydrochloride of compound (1) of the present invention had been administered, the occurrence of emesis was completely suppressed. From these results, it is concluded that compounds (1) of the present invention are useful for preventing and treating motion sickness, emesis, space sickness, dizziness and the like.

3. Activity to suppress the drug-induced emesis

It has been known that cisplatin and nicotine have an emesis-inducing activity. In this test, it was investigated as to whether the hydrochloride of compound (1) of the present invention has the activity to suppress the occurrence of emeses which are induced by these drugs.

Cisplatin was intraperitoneally administered to each of four suncuses (20 mg/kg). As a result, with respect to all of the suncuses, emesis occurred 10 to 20 times within 40 to 70 minutes after the administration of the cisplatin. However, when compound 300 of the present invention (in the form of the hydrochloride thereof) was intraperitoneally administered to the suncuses (0.3 mg/kg) 30 minutes before the administration of cisplatin, the occurrence of cisplatin-induced emesis was completely suppressed.

On the other hand, nicotine was subcutaneously administered to four suncuses (4 mg/kg). As a result, with respect to all of the suncuses, emesis was induced 11 to 29 times within 3 to 10 minutes after the administration of the nicotine. However, when compound 300 of the present invention (in the form of the hydrochloride thereof) was intraperitoneally administered to the suncuses (3 mg/kg) 30 minutes before the administration of nicotine, the occurrence of nicotine-induced emesis was completely suppressed.

Cisplatin has long been used as a carcinostatic substance. However, there is a serious problem in that cisplatin induces emesis as a side effect. Since compound (1) of the present invention can suppress the occurrence of cisplatin-induced emesis, it is concluded that compound (1) of the present invention is effective for preventing emesis which is caused by the administration of a carcinostatic substance. At present, it is known that although certain drugs, such as ondansetron (which is a 5-HT3 blocking agent), are effective for suppressing cisplatin-induced emesis, they have no effect on emesis induced by drugs other than cisplatin or on motion sickness. By contrast, as demonstrated above, compound 300 of the present invention (in the form of the hydrochloride thereof) is effective for suppressing nicotine-induced emesis and motion sickness as well as cisplatin-induced emesis and, therefore, compound 300 of the present invention can be used as an excellent antiemetic agent for various purposes.

4. Anti-depression activity (which was evaluated by forced swimming test using rats)

When a rat is put in a water tank, the rat struggles for its life to get out of the water (that is, the rat starts a "forced swimming"). If the rat finds that it is impossible for him to get out, the rat stops swimming and assumes an immobile state. It has been known that the administration of an antidepressant can cause a violent swimming motion in the rat for getting out of the water, with a result that the time spent in the immobile state is shortened. The shortening of the time in the immobile state of the rat in the forced swimming test by the administration of the antidepressant is well correlated to the clinical anti-depression effect. Accordingly, in developing antidepressants, the forced swimming test using a rat is the most reliable screening method. In the present test, male Wistar strain rats were used. Compound 300 of the present invention (in the form of the hydrochloride thereof) was intraperitoneally administered to a rat. 30 minutes after the administration, the rat was put in a water tank and then, observed for 6 minutes. The time for the rat to keep the immobile state was measured.

As shown in Table 4 below, compound 300 of the present invention (in the form of the hydrochloride thereof; 1 mg/kg and 10 mg/kg) remarkably shortened the time for the rat to keep the immobile state. From these results, it is concluded that compound 300 of the present invention is effective for preventing and treating depression.

TABLE 4

| Test compound | Dose | Time spent in immobile state | Number of tested rats |
| --- | --- | --- | --- |
| Physiological saline (control) | | 236 sec. | 8 |
| 300 (hydrochloride) | 1 mg/kg | 173 sec. | 6 |
| | 10 mg/kg | 163 sec. | 6 |

Further, when each of compounds (1) of the present invention synthesized in Examples (each in the form of the hydrochloride thereof) was intraperitoneally administered to three mice (50 mg/kg), none of the mice died. The results indicate that compounds (1) of the present invention are highly safe.

From the above results, it will be understood that compound (1) of the present invention (in the form of the hydrochloride thereof) has a strong affinity for the serotonin 1A receptor, and are useful for prevention and treatment of a serotonergic neuron-related disease, such as motion sickness, space sickness, emesis, dizziness, depression, anxiety, eating disorder or the like.

BEST MODE FOR CARRYING OUT THE INVENTION

The present invention will be described in greater detail with reference to the following Reference Examples and Examples, in respect of desired compounds (1) and hydrochlorides thereof, production methods thereof, and intermediates for the synthesis of compounds (1).

Physical properties (i.e., NMR spectra and mass spectra) of the compounds obtained in the following Reference Examples and Examples are shown in Tables 9 and 10 below.

Reference Example 1

2-Hydroxy-5,6,7,8-tetrahydroquinoxaline 11.05 g (0.1 mol) of glycinamide hydrochloride was dissolved in 200 ml of methanol. To the resultant solution was added a solution of 13.44 g (0.12 mol) of cyclohexane-1,2-dione in 30 ml of methanol under cooling to −30° C. or lower and then, 20 ml of an aqueous 12.5 N NaOH solution was dropwise added thereto. Subsequently, the resultant mixture was stirred at −30° C. or lower for 30 minutes and further stirred at room temperature for 3 hours to effect a reaction. To the resultant reaction mixture was added 25 ml of concentrated hydrochloric acid, followed by stirring for 10 minutes and then, 15 g of sodium hydrogencarbonate was added thereto. The solvent of the reaction mixture was distilled off in vacuo to thereby obtain a residue. Water was added-to the obtained residue, followed by extraction with chloroform three times to obtain an extract. The extract was dried over anhydrous magnesium sulfate and concentrated in vacuo. The resultant residue was recrystallized from acetone, to thereby obtain 9.36 g of 2-hydroxy-5,6,7,8-tetrahydroquinoxaline (yield: 62.4%).

Reference Example 2

2-(3-Ethoxycarbonylpropoxy)-5,6,7,8-tetrahydroquinoxaline 1.5 g (10 mmol) of 2-hydroxy-5,6,7,8-tetrahydroquinoxaline was dissolved in 30 ml of methanol. To the resultant solution was added 10 ml of a 1N solution of sodium methoxide in methanol to effect a reaction. The solvent of the resultant reaction mixture was distilled off in vacuo to thereby obtain a sodium salt of 2-hydroxy-5,6,7,8-tetrahydroquinoxaline. The sodium salt was dissolved in 30 ml of N,N-dimethylformamide (DMF), and 1.95 g (10 mmol) of ethyl 4-bromobutyrate was added thereto. The resultant mixture was stirred with heating at 100° C. overnight to effect a reaction. The solvent of the resultant reaction mixture was distilled off in vacuo to thereby obtain a residue. Water was added to the obtained residue, followed by extraction with chloroform twice to obtain an extract. The extract was dried over mirabilite, and the solvent was distilled off to thereby obtain a residue. The obtained residue was purified by silica gel column chromatography. That is, the residue was charged in a column of 40 g of silica gel (C-200, manufactured and sold by Wako Pure Chemical Industries, Ltd.) and eluted with toluene-ethyl acetate (10:1), to thereby obtain 1.59 g of 2-(3-ethoxycarbonylpropoxy)-5, 6,7,8-tetrahydroquinoxaline (yield: 60.3%).

Reference Examples 3 to 6

3-Alkyl-2-(3-ethoxycarbonylpropoxy)-5,6,7,8-tetrahydroquinoxalines

Substantially the same procedure as in Reference Example 2 was repeated except that four types of 3-alkyl-2-hydroxy-5,6,7,8-tetrahydroquinoxalines were individually used instead of 2-hydroxy-5,6,7,8-tetrahydroquinoxaline, to thereby obtain four types of 3-alkyl-2-(3-ethoxycarbonylpropoxy)-5,6,7,8-tetrahydroquinoxalines corresponding thereto. The amounts of the 3-alkyl-2-hydroxy-5,6,7,8-tetrahydroquinoxalines used are shown in Table 5, together with the amounts and yields of the desired 3-alkyl-2-(3-ethoxycarbonylpropoxy)-5,6,7,8-tetrahydroquinoxalines produced.

TABLE 5

[Structure: tetrahydroquinoxaline with N-OH and N-R¹ → tetrahydroquinoxaline with O-(CH₂)₃-COOC₂H₅ and R¹]

| Reference Example No. | R¹ | Amount of 2-*[1] hydroxy compound used (g) | Product Amount (g) | Product Yield (%) |
|---|---|---|---|---|
| 3 | CH₃ | 1.64 | 1.73 | 62.1 |
| 4 | C₃H₇ | 2.30 | 2.13 | 58.0 |
| 5 | iso-C₃H₇ | 2.30 | 1.91 | 52.0 |
| 6 | C₅H₁₁ | 2.20 | 2.31 | 69.2 |

*[1]Note: 2-hydroxy compound means a 3-alkyl-2-hydroxy-5,6,7,8-tetrahydroquinoxaline.

Reference Example 7

2-(4-Hydroxybutoxy)-5,6,7,8-tetrahydroquinoxaline

1.84 g (7.0 mmol) of 2-(3-ethoxycarbonylpropoxy)-5,6,7,8-tetrahydroquinoxaline was dissolved in 10 ml of tetrahydrofuran (THF), and the solution was ice-cooled. The resultant solution was dropwise added to a suspension of 319 mg (8.4 mmol) of lithium aluminum hydride in 15 ml of THF under ice cooling, followed by stirring for 2 hours at the same temperature as used in the ice cooling above, to thereby effect a reaction. To the resultant reaction mixture was added 2N HCl to thereby acidify the mixture and form a precipitate. The resultant mixture was subjected to filtration to filter off the precipitate, which was then washed with water. The filtrate was extracted with chloroform twice to obtain an extract. The extract was dried over mirabilite, and the solvent was distilled off in vacuo. The resultant residue was purified by silica gel column chromatography. That is, the residue was charged in a column of 50 g of silica gel (C-200, manufactured and sold by Wako Pure Chemical Industries, Ltd.) and eluted with chloroform-methanol (200:1), to thereby obtain 1.55 g of 2-(4-hydroxybutoxy)-5,6,7,8-tetrahydroquinoxaline (yield: 100%).

Reference Examples 8 to 11

3-Alkyl-2-(4-hydroxybutoxy)-5,6,7,8-8-tetrahydroquinoxalines

Substantially the same procedure as in Reference Example 7 was repeated except that four types of 3-alkyl-2-(3-ethoxycarbonylpropoxy)-5,6,7,8-tetrahydroquinoxalines were individually used instead of 2-(3-ethoxycarbonylpropoxy)-5,6,7,8-tetrahydroquinoxaline, to thereby obtain four types of 3-alkyl-2-(4-hydroxybutoxy)-5,6,7,8-tetrahydroquinoxalines corresponding thereto.

The amounts of the 3-alkyl-2-(3-ethoxycarbonylpropoxy)-5,6,7,8-tetrahydroquinoxalines used are shown in Table 6, together with the amounts and yields of the desired 3-alkyl-2-(4-hydroxybutoxy)-5,6,7,8-tetrahydroquinoxalines produced.

TABLE 6

[Structure: tetrahydroquinoxaline with O-(CH₂)₃-COOC₂H₅ and R¹ → tetrahydroquinoxaline with O-(CH₂)₄-OH and R¹]

| Reference Example No. | R¹ | Amount of*[2] ester compound used (g) | Product Amount (g) | Product Yield (%) |
|---|---|---|---|---|
| 8 | CH₃ | 1.56 | 1.32 | 100 |
| 9 | C₃H₇ | 1.98 | 1.44 | 82.4 |
| 10 | iso-C₃H₇ | 2.14 | 1.83 | 97.8 |
| 11 | C₅H₁₁ | 1.78 | 1.51 | 98.3 |

*[2]Note: Ester compound means a 3-alkyl-2-(3-ethoxy-carbonylpropoxy)-5,6,7,8-tetrahydroquinoxaline.

Reference Example 12

2-(4-Methanesulfonyloxybutoxy)-5,6,7,8-tetrahydroquinoxaline

1.55 g (6.98 mmol) of 2-(4-hydroxybutoxy)-5,6,7,8-tetrahydroquinoxaline was dissolved in 30 ml of methylene chloride, and the solution was ice-cooled. To the resultant solution was added 1.17 ml (8.4 mmol) of triethylamine and then, 0.59 ml (7.7 mmol) of methanesulfonyl chloride was dropwise added thereto. The resultant mixture was stirred for 2.5 hours at the same temperature as used in the ice cooling above, to thereby by effect a reaction. To the resultant reaction mixture was added 20 ml of chloroform to obtain a mixture. The mixture was extracted with an aqueous solution of diluted sodium carbonate to thereby obtain an organic layer and an aqueous layer. The aqueous layer was subjected to extraction with chloroform to obtain an additional organic layer. The two organic layers were combined and dried over mirabilite and then, the solvent of the resultant organic layer was distilled off in vacuo, to thereby obtain 1.92 g of 2-(4-methanesulfonyloxybutoxy)-5,6,7,8-tetrahydroquinoxoline (yield: 91.7%).

Reference Examples 13 to 16

3-Alkyl-2-(4-methanesulfonyloxybutoxy)-5,6,7,8-tetrahydroquinoxalines

Substantially the same procedure as in Reference Example 12 was repeated except that four types of 3-alkyl-2-(4-hydroxybutoxy)-5,6,7,8-tetrahydroquinoxlines were individually used instead of 2-(4-hydroxybutoxy)-5,6,7,8-tetrahydroquinoxaline, to thereby obtain four types of 3-alkyl-2-(4-methanesulfonyloxybutoxy)-5,6,7,8-tetrahydroquinoxalines corresponding thereto. The amounts of the 3-alkyl-2-(4-hydroxybutoxy)-5,6,7,8-tetrahydroquinoxalines used are shown in Table 7, together with the amounts and yields of the desired 3-alkyl-2-(4-methanesulfonyloxybutoxy)-5,6,7,8-tetrahydroquinoxalines produced.

TABLE 7

[Reaction scheme: 2-alkyl-3-(4-hydroxybutoxy)-5,6,7,8-tetrahydroquinoxaline → 2-alkyl-3-(4-methanesulfonyloxybutoxy)-5,6,7,8-tetrahydroquinoxaline, with substituent $R^1$]

| Reference Example No. | $R^1$ | Amount of*[3] hydroxy compound used (g) | Product Amount (g) | Yield (%) |
|---|---|---|---|---|
| 13 | $CH_3$ | 1.47 | 1.74 | 89.1 |
| 14 | $C_3H_7$ | 1.30 | 1.59 | 94.1 |
| 15 | iso-$C_3H_7$ | 1.43 | 1.86 | 100 |
| 16 | $C_5H_{11}$ | 1.68 | 1.99 | 93.4 |

*[3]Note: Hydroxy compound means a 3-alkyl-2-(4-hydroxybutoxy)-5,6,7,8-tetrahydroquinoxaline.

Reference Example 17

2-(4-Chlorobutoxy)-5,6,7,8-tetrahydroquinoxaline 300 mg (2 mmol) of 2-hydroxy-5,6,7,8-tetrahydroquinoxaline was dissolved in 5 ml of DMF, and 360 μl (2.4 mmol) of 1,8-diazabicyclo[5.4.0]undeca-7-ene (DBU) and 277 μl (2.4 mmol) of 1-bromo-4-chlorobutane were added thereto. The resultant mixture was stirred with heating at 60° C. for 22 hours to effect a reaction. The DMF in the resultant reaction mixture was distilled off in vacuo to thereby obtain a residue. An aqueous solution of potassium carbonate was added to the obtained residue, followed by extraction with chloroform to obtain an extract. The extract was dried over sodium sulfate anhydride, and subjected to filtration to thereby obtain a filtrate. The solvent of the filtrate was distilled off to thereby obtain a residue. The obtained residue was purified by silica gel column chromatography. That is, the residue was charged in a column of 20 g of silica gel (Art7734, manufactured and sold by E. Merck, Darmstadt) and eluted with chloroform, to thereby obtain 263 mg of 2-(4-chlorobutoxy)-5,6,7,8-tetrahydroquinoxaline (yield: 54.7%).

Reference Example 18

2-(4-Chlorobutoxy)-3-isopropyl-5,6,7,8-tetrahydroquinoxaline

Substantially the same procedure as in Reference Example 17 was repeated except that 384 mg (2 mmol) of 2-hydroxy-3-isopropyl-5,6,7,8-tetrahydroquinoxaline was used instead of 2-hydroxy-5,6,7,8-tetrahydroquinoxaline, to thereby obtain 287 mg of 2-(4-chlorobutoxy)-3-isopropyl-5,6,7,8-tetrahydroquinoxaline (yield: 50.8%).

Reference Example 19

2-Ethoxycarbonylmethoxy-5,6,7,8-tetrahydroquinoxaline

Substantially the same procedure as in Reference Example 2 was repeated except that 1.67 g (10 mmol) of ethyl bromoacetate was used instead of ethyl 4-bromobutyrate, to thereby obtain 4.04 g of 2-ethoxycarbonyl-methoxy-5,6,7,8-tetrahydroquinoxaline (yield: 86%).

Reference Example 20

2-(2-Hydroxyethoxy)-5,6,7,8-tetrahydroquinoxaline

Substantially the same procedure as in Reference Example 7 was repeated except that 1.65 g (7 mmol) of 2-ethoxycarbonylmethoxy-5,6,7,8-tetrahydroquinoxaline was used instead of 2-(3-ethoxycarbonylpropoxy)-5,6,7,8-tetrahydroquinoxaline, to thereby obtain 0.95 g of 2-(2-hydroxyethoxy)-5,6,7,8-tetrahydroquinoxaline (yield: 70%).

Reference Example 21

2-(3-Chloropropoxy)-5,6,7,8-tetrahydroquinoxaline 1.5 g (10 mmol) of 2-hydroxy-5,6,7,8-tetrahydroquinoxaline was dissolved in 40 ml of acetonitrile. To the resultant solution were added 2.76 g (20 mmol) of potassium carbonate and 1.19 ml (12 mmol) of 1-bromo-3-chloropropane. The resultant mixture was heated under reflux for 2 hours and then, subjected to filtration to thereby filter off insoluble substances. The solvent of the filtrate was distilled off in vacuo to thereby obtain a residue. The obtained residue was purified by silica gel column chromatography. That is, the residue was charged in a column of 42 g of silica gel (Art7734, manufactured and sold by E. Merck, Darmstadt) and eluted with chloroform, to thereby obtain 1.47 g of 2-(3-chloropropoxy)-5,6,7,8-tetrahydroquinoxaline (yield: 67%).

Reference Example 22

2-(5-Chloropentoxy)-5,6,7,8-tetrahydroquinoxaline

Substantially the same procedure as in Reference Example 21 was repeated except that 1.58 ml (12 mmol) of 1-bromo-5-chloropentane was used instead of 1-bromo-3-chloropropane, to thereby obtain 2.46 g of 2-(5-chloropentoxy)-5,6,7,8-tetrahydroquinoxaline (yield: 97%).

EXAMPLE 1

2-[4-{4-(2-Pyridyl)-1-piperazinyl}butoxy]-5,6,7,8-tetrahydroquinoxaline (compound 300)

300 mg (1 mmol) of 2-(4-methanesulfonyloxybutoxy)-5,6,7,8-tetrahydroquinoxaline was dissolved in 10 ml of acetonitrile. To the resultant solution were added 208 mg (1.5 mmol) of potassium carbonate and 196 mg (1.2 mmol) of 1-(2-pyridyl)piperazine, and the resultant mixture was heated under reflux for 15 hours. Then, the mixture was subjected to filtration to filter off insoluble substances, which were then washed with acetonitrile, to thereby obtain a filtrate. The solvent of the filtrate was distilled off in vacuo to thereby obtain a residue. The obtained residue was purified by silica gel column chromatography. That is, the residue was charged in a column of 20 g of silica gel (Art7734, manufactured and sold by E. Merck, Darmstadt) and eluted with chloroform-methanol (100:1), to thereby obtain 293 mg of 2-[4-{4-(2-pyridyl)-1-piperazinyl}-butoxy]-5,6,7,8-tetrahydroquinoxaline (compound 300) (yield: 79.8%).

The obtained 2-[4-{4-(2-pyridyl)-1-piperazinyl}butoxy]-5,6,7,8-tetrahydroquinoxaline was dissolved in a solution of 8.9N hydrochloric acid in methanol. To the resultant solution was added diethyl ether, to thereby crystallize a solid substance in the solution. The resultant solution was subjected to filtration, to thereby obtain the hydrochloride of 2-[4-{4-(2-pyridyl)-1piperazinyl}butoxy]-5,6,7,8-tetrahydroquinoxaline.

EXAMPLE 2

2-[4-{4-(2-Pyrimidinyl)-1-piperazinyl}butoxy]-5,6,7,8-tetrahydroquinoxaline (compound 301)

Substantially the same procedure as in Example 1 was repeated, except that 197 mg (1.2 mmol) of 1-(2-pyrimidinyl)piperazine was used instead of 1-(2-pyridyl)piperazine, to thereby obtain 158 mg of 2-[4-{4-(2-pyrimidinyl)-1-piperazinyl}butoxy]-5,6,7,8-tetrahydroquinoxaline (compound 301) (yield: 42.9%).

In substantially the same manner as in Example 1, the hydrochloride of the obtained 2-[4-{4-(2-pyrimidinyl)-1-piperazinyl}butoxy]-5,6,7,8-tetrahydroquinoxaline was obtained.

EXAMPLES 3 to 10

2-[4-{4-(2-Pyridyl)-1-piperazinyl}butoxy]-3-alkyl-5,6,7,8-tetrahydroquinoxalines and 2-[4-{4-(2-pyrimidinyl)-1-piperazinyl}butoxy]-3-alkyl-5,6,7,8-tetrahydroquinoxalines (compounds 409, 410, 423, 414, 431, 432, 425 and 428)

Substantially the same procedures as in Examples 1 and 2 were repeated, in which the four types of 2-(4-methanesulfonyloxybutoxy)-3-alkyl-5,6,7,8-tetrahydroquinoxalines were used instead of 2-(4-methanesulfonyloxybutoxy)-5,6,7,8-tetrahydroquinoxalines, and reacted with each of 1-(2-pyridyl)piperazine and 1-(2-pyrimidinyl)piperazine, to thereby obtain four types of 2-[4-{4-(2-pyridyl)-1-piperazinyl}butoxy]-3-alkyl-5,6,7,8-tetrahydroquinoxalines and four types of 2-[4-{4-(2-pyrimidinyl)-1-piperazinyl}butoxy]-3-alkyl-5,6,7,8-tetrahydroquinoxalines (compounds 409, 410, 423, 414, 431, 432, 435 and 428) corresponding thereto.

The hydrochlorides of the obtained 2-[4-{4-(2-pyridyl)-1-piperazinyl}butoxy]-3-alkyl-5,6,7,8-tetrahydroquinoxalines and 2-[4-{4-(2-pyrimidinyl)-1-piperazinyl}butoxy]-3-alkyl-5,6,7,8-tetrahydroquinoxalines were obtained in the same manner as in Example 1.

The amounts of the 3-alkylated compounds (2') [2-(4-methanesulfonyloxybutoxy)-3-alkyl-5,6,7,8-tetrahydroquinoxalines] and piperazine derivatives (3) [1-(2-pyridyl)piperazine and 1-(2-pyrimidinyl)piperazine] used are shown in Table 8, together with the amounts and yields of the desired 2-[4-{4-(2-pyridyl)-1-piperazinyl}butoxy]-3-alkyl-5,6,7,8-tetrahydroquinoxalines and 2-[4-{4-(2-pyrimidinyl)-1-piperazinyl}butoxy]-3-alkyl-5,6,7,8-tetrahydroquinoxalines produced.

TABLE 8

[Reaction scheme: compound (2') with $OCH_2CH_2CH_2CH_2OSO_2CH_3$ group and $R^1$ substituent + piperazine derivative (3) HN-N-$R^2$ → compound (1') with $OCH_2CH_2CH_2CH_2$-N-N-$R^2$ group and $R^1$ substituent]

| Example No. | 3-alkylated compound (2') $R^1$ (Amount used) | Piperazine derivative (3) $R^2$ (Amount used) | Desired compound (1') Compound No. | Amount (mg) Yield (%) |
|---|---|---|---|---|
| 3 | $CH_3$ (314 mg) | 2-pyridyl (196 mg) | 409 | 327 mg 85.7% |
| 4 | $CH_3$ (314 mg) | 2-pyrimidinyl (197 mg) | 410 | 361 mg 94.5% |
| 5 | $C_3H_7$ (342 mg) | 2-pyridyl (196 mg) | 423 | 384 mg 93.9% |
| 6 | $C_3H_7$ (342 mg) | 2-pyrimidinyl (197 mg) | 414 | 383 mg 93.3% |
| 7 | iso-$C_3H_7$ (342 mg) | 2-pyridyl (196 mg) | 431 | 375 mg 91.6% |
| 8 | iso-$C_3H_7$ (342 mg) | 2-pyrimidinyl (197 mg) | 432 | 406 mg 99.1% |
| 9 | $C_5H_{11}$ (370 mg) | 2-pyridyl (196 mg) | 425 | 389 mg 89.1% |
| 10 | $C_5H_{11}$ (370 mg) | 2-pyrimidinyl (197 mg) | 428 | 413 mg 94.4% |

EXAMPLE 11

2-[4-{4-(2-Pyridyl)-1-piperazinyl}butoxy]-5,6,7,8-tetrahydroquinoxaline (compound 300).

Substantially the same procedure as in Example 1 was repeated, except that 241 mg (1 mmol) of 2-(4-chlorobutoxy)-5,6,7,8-tetrahydroquinoxaline was used instead of 2-(4-methanesulfonyloxybutoxy)-5,6,7,8-tetrahydroquinoxaline, and that 149 mg (1 mmol) of sodium iodide was added thereto, to thereby obtain 148 mg of 2-[4-{4-(2-pyridyl)-1-piperazinyl}butoxy]-5,6,7,8-tetrahydroquinoxaline (compound 300) (yield: 40.4%).

EXAMPLE 12

2-[4-{4-(4,6-Dimethyl-2-pyrimidinyl)-1-piperazinyl}-butoxy]-5,6,7,8-tetrahydroquinoxaline (compound 481)

241 mg (1 mmol) of 2-(4-chlorobutoxy)-5,6,7,8-tetrahydroquinoxaline was dissolved in 10 ml of acetonitrile. To the resultant solution were added 208 mg (1.5 mmol) of potassium carbonate and 230 mg (1.2 mmol) of 1-(4,6-dimethyl-2-pyrimidinyl)piperazine, and the resultant mixture was heated under reflux for 15 hours. Then, the mixture was subjected to filtration to filter off insoluble substances, which were then washed with acetonitrile, to thereby obtain a filtrate. The solvent of the filtrate was distilled off in vacuo to thereby obtain a residue. The obtained residue was purified by silica gel column chromatography. That is, the residue was charged in a column of 20 g of silica gel (Art7734, manufactured and sold by E. Merck, Darmstadt) and eluted with chloroform-methanol (100:1), to thereby obtain 191 mg of 2-[4-{4-(4,6-dimethyl-2-pyrimidinyl)-1-piperazinyl}butoxy]-5,6,7,8-tetrahydroquinoxaline (compound 481) (yield: 48.2%).

In substantially the same manner as in Example 1, the hydrochloride of the obtained 2-[4-{4-(4,6-dimethyl2-pyrimidinyl)-1-piperazinyl}butoxy]-5,6,7,8-tetrahydroquinoxaline was obtained.

EXAMPLE 13

2-[4-{4-(6-Methyl-2-pyridyl)-1-piperazinyl}butoxy]-5,6,7,8-tetrahydroquinoxaline (compound 501)

241 mg (1 mmol) of 2-(4-chlorobutoxy)-5,6,7,8-tetrahydroquinoxaline was dissolved in 10 ml of acetonitrile. To the resultant solution were added 208 mg (1.5 mmol) of potassium carbonate, 212 mg (1.2 mmol) of 1-(6-methyl-2-pyridyl)piperazine and 149 mg (1 mmol) of sodium iodide, and the resultant mixture was heated under reflux for 15 hours. Then, the mixture was subjected to filtration to filter off insoluble substances, which were then washed with acetonitrile, to thereby obtain a filtrate. The solvent of the filtrate was distilled off in vacuo to thereby obtain a residue. The obtained residue was purified by silica gel column chromatography. That is, the residue was charged in a column of 20 g of silica gel (Art7734, manufactured and sold by E. Merck, Darmstadt) and eluted with chloroform-methanol (100:1), to thereby obtain 129 mg of 2-[4-{4-(6-methyl-2-pyridyl)-1-piperazinyl}butoxy]-5,6,7,8-tetrahydroquinoxaline (compound 501) (yield: 34%).

In substantially the same manner as in Example 1, the hydrochloride of the obtained 2-[4-{4-(6-methyl-2-pyridyl)-1-piperazinyl}butoxy]-5,6,7,8-tetrahydroquinoxaline was obtained.

EXAMPLE 14

2-[4-{4-(3-Chloro-2-pyridyl)-1-piperazinyl}butoxy]-5,6,7,8-tetrahydroquinoxaline (compound 502)

Substantially the same procedure as in Example 13 was repeated, except that 237 mg (1.2 mmol) of 1-(3-chloro-2-pyridyl)piperazine was used instead of 1-(6-methyl-2-pyridyl)piperazine, to thereby obtain 171 mg of 2-[4-{4-(3-chloro-2-pyridyl)-1-piperazinyl}butoxy]-5,6,7,8-tetrahydroquinoxaline (compound 502) (yield: 45%).

In substantially the same manner as in Example 1, the hydrochloride of the obtained 2-[4-{4-(3-chloro-2-pyridyl)-1-piperazinyl}butoxy]-5,6,7,8-tetrahydroquinoxaline was obtained.

EXAMPLE 15

2-[4-{4-(3-Methoxy-2-pyridyl)-1-piperazinyl}-butoxy]-5,6,7,8-tetrahydroquinoxaline (compound 557), Substantially the same procedure as in Example 13 was repeated, except that 232 mg (1.2 mmol) of 1-(3-methoxy-2-pyridyl)piperazine was used instead of 1-(6-methyl-2-pyridyl)piperazine, to thereby obtain 179 mg of 2-[4-{4-(3-methoxy-2-pyridyl)-1-piperazinyl}butoxy]-5,6,7,8-tetrahydroquinoxaline (compound 557) (yield: 45%).

In substantially the same manner as in Example 1, the hydrochloride of the obtained 2-[4-{4-(3-methoxy-2-pyridyl-1-piperazinyl}butoxy]-5,6,7,8-tetrahydroquinoxaline was obtained.

EXAMPLE 16

2-[4-{4-(3-Cyano-2-pyridyl)-1-piperazinyl}butoxy]-5,6,7,8-tetrahydroquinoxaline (compound 514)

Substantially the same procedure as in Example 13 was repeated, except that 226 mg (1.2 mmol) of 1-(3-cyano-2pyridyl)piperazine was used instead of 1-(6-methyl-2-pyridyl)piperazine, to thereby obtain 309 mg of 2-[4-{4-(3-cyano-2-pyridyl)-1-piperazinyl}butoxy]-5,6,7,8-tetrahydroquinoxaline (compound 514) (yield: 79%).

In substantially the same manner as in Example 1, the hydrochloride of the obtained 2-[4-{4-(3-cyano-2-pyridyl)-1-piperazinyl}butoxy]-5,6,7,8-tetrahydroquinoxaline was obtained.

EXAMPLE 17

2-[4-{4-(3,6-Dimethyl-2-pyridyl)-1-piperazinyl}-butoxy]-5,6,7,8-tetrahydroquinoxaline (compound 598)

Substantially the same procedure as in Example 13 was repeated, except that 229 mg (1.2 mmol) of 1-(3,6-dimethyl-2-pyridyl)piperazine was used instead of 1-(6-methyl-2-pyridyl)piperazine, to thereby obtain 113 mg of 2-[4-{4-(3,6-dimethyl-2-pyridyl)-1-piperazinyl}butoxy]-5,6,7,8-tetrahydroquinoxaline (compound 598) (yield: 30%).

In substantially the same manner as in Example 1, the hydrochloride of the obtained 2-[4-{4-(3,6-dimethyl-2-pyridyl)-1-piperazinyl}butoxy]-5,6,7,8-tetrahydroquinoxaline was obtained.

EXAMPLE 18

2-[4-{4-(6-Chloro-2-pyridyl)-1-piperazinyl}butoxy]-5,6,7,8-tetrahydroquinoxaline (compound 500)

Substantially the same procedure as in Example 13 was repeated, except that 237 mg (1.2 mmol) of 1-(6-chloro-2-pyridyl)piperazine was used instead of 1-(6-methyl-2-pyridyl)piperazine, to thereby obtain 108 mg of 2-[4-{4-(6-chloro-2-pyridyl)-1-piperazinyl}butoxy]-5,6,7,8-tetrahydroquinoxaline (compound 500) (yield: 27%).

In substantially the same manner as in Example 1, the hydrochloride of the obtained 2-[4-{4-(6-chloro-2-pyridyl)-1-piperazinyl}butoxy]-5,6,7,8-tetrahydroquinoxaline was obtained.

EXAMPLE 19

2-[4-{4-(6-Ethoxy-2-pyridyl)-1-piperazinyl}butoxy]-5,6,7,8-tetrahydroquinoxaline (compound 524)

Substantially the same procedure as in Example 13 was repeated, except that 248 mg (1.2 mmol) of 1-(6-ethoxy-2-pyridyl)piperazine was used instead of 1-(6-methyl-2-pyridyl)piperazine, to thereby obtain 282 mg of 2-[4-{4-(6-ethoxy-2-pyridyl)-1-piperazinyl}butoxy]-5,6,7,8-tetrahydroquinoxaline (compound 524) (yield: 69%).

In substantially the same manner as in Example 1, the hydrochloride of the obtained 2-[4-{4-(6-ethoxy-2-pyridyl)-1-piperazinyl}butoxy]-5,6,7,8-tetrahydroquinoxaline was obtained.

EXAMPLE 20

2-[4-{4-(3-Carbamoyl-2-pyridyl)-1-piperazinyl}-butoxy]-5,6,7,8-tetrahydroquinoxaline (Compound 526)

Substantially the same procedure as in Example 13 was repeated, except that 245 mg (1.2 mmol) of 1-(3-carbamoyl-2-pyridyl)piperazine was used instead of 1-(6-methyl-2-pyridyl)piperazine, to thereby obtain 302 mg of 2-[4-{4-(3-carbamoyl-2-pyridyl)-1-piperazinyl}butoxy]-5,6,7,8-tetrahydroquinoxaline (compound 526) (yield: 74%).

In substantially the same manner in Example 1, the hydrochloride of the obtained 2-[4-{4-(3-carbamoyl-2-pyridyl)-1-piperazinyl}butoxy]-5,6,7,8-tetrahydroquinoxaline was obtained.

EXAMPLE 21

2-[4-{4-(6-Methoxy-2-pyridyl)-1-piperazinyl}-butoxy]-5,6,7,8-tetrahydroquinoxaline (compound 539)

Substantially the same procedure as in Example 13 was repeated, except that 232 mg (1.2 mmol) of 1-(6-methoxy-2-pyridyl)piperazine was used instead of 1-(6-methyl-2-pyridyl)piperazine, to thereby obtain 336 mg of 2-[4-{4-(6-methoxy-2-pyridyl)-1-piperazinyl}butoxy]-5,6,7,8-tetrahydroquinoxaline (compound 539) (yield: 85%).

In substantially the same manner as in Example 1, the hydrochloride of the obtained 2-[4-{4-(6-methoxy-2-pyridyl)-1-piperazinyl}butoxy]-5,6,7,8-tetrahydroquinoxaline was obtained.

EXAMPLE 22

2-[4-{4-(3-Cyano-4-6-dimethyl-2-pyridyl)-1-piperazinyl}butoxy]-5,6,7,8-tetrahydroquinoxaline (compound 561)

Substantially the same procedure as in Example 13 was repeated, except that 259 mg (1.2 mmol) of 1-(3-cyano-4,6-dimethyl-2-pyridyl)piperazine was used instead of 1-(6-methyl-2-pyridyl)piperazine, to thereby obtain 192 mg of 2-[4-{4-(3-cyano-4,6-dimethyl-2-pyridyl)-1-piperazinyl}butoxy]-5,6,7,8-tetrahydroquinoxaline (compound 561) (yield: 46%).

In substantially the same manner as in Example 1, the hydrochloride of the obtained 2-[4-{4-(3-cyano-4,6-dimethyl-2-pyridyl)-1-piperazinyl}butoxy]-5,6,7,8-tetrahydroquinoxaline was obtained.

EXAMPLE 23

2-[4-{4-(4,6-Dimethyl-2-pyridyl)-1-piperazinyl}-butoxy]-5,6,7,8-tetrahydroquinoxaline (compound 569)

Substantially the same procedure as in Example 13 was repeated, except that 229 mg (1.2 mmol) of 1-(4,6-dimethyl-2-pyridyl)piperazine was used instead of 1-(6-methyl-2-pyridyl)piperazine, to thereby obtain 216 mg of 2-[4-{4-(4,6-dimethyl-2-pyridyl)-1-piperazinyl}butoxy]-5,6,7,8-tetrahydroquinoxaline (compound 569) (yield: 66%).

In substantially the same manner as in Example 1, the hydrochloride of the obtained 2-[4-{4-(4,6-dimethyl-2-pyridyl)-1-piperazinyl}butoxy]-5,6,7,8-tetrahydroquinoxaline was obtained.

EXAMPLE 24

2-[4-{4-(3-Trifluoromethyl-2-pyridyl)-1-piperazinyl}-butoxy]-5,6,7,8-tetrahydroquinoxaline (compound 621)

Substantially the same procedure as in Example 13 was repeated, except that 277 mg (1.2 mmol) of 1-(3-trifluoromethyl-2-pyridyl)piperazine was used instead of 1-(6-methyl-2-pyridyl)piperazine, to thereby obtain 359 mg of 2-[4-{4-(3-trifluoromethyl-2-pyridyl)-1-piperazinyl}butoxy]-5,6,7,8-tetrahydroquinoxaline (compound 621) (yield: 83%).

In substantially the same manner as in Example 1, the hydrochloride of the obtained 2-[4-{4-(3-trifluoromethyl-2-pyridyl)-1-piperazinyl}butoxy]-5,6,7,8-tetrahydroquinoxaline was obtained.

EXAMPLE 25

2-[4-{4-(6-Propoxy-2-pyridyl)-1-piperazinyl}butoxy]-5,6,7,8-tetrahydroquinoxaline (compound 629)

Substantially the same procedure as in Example 13 was repeated, except that 265 mg (1.2 mmol) of 1-(6-propoxy-2-pyridyl)piperazine was used instead of 1-(6-methyl-2-pyridyl)piperazine, to thereby obtain 257 mg of 2-[4-{4-(6-propoxy-2-pyridyl)-1-piperazinyl}butoxy]-5,6,7,8-tetrahydroquinoxaline (compound 629) (yield: 61%).

In substantially the same manner as in Example 1, the hydrochloride of the obtained 2-[4-{4-(6-propoxy-2-pyridyl)-1-peperazinyl}butoxy]-5,6,7,8-tetrahydroquinoxaline was obtained.

EXAMPLE 26

2-[4-{4-(6-Isopropoxy-2-pyridyl)-1-piperazinyl}-butoxy]-5,6,7,8-tetrahydroquinoxaline (compound 630)

Substantially the same procedure as in Example 13 was repeated, except that 265 mg (1.2 mmol) of 1-(6-isopropoxy-2-pyridyl)piperazine was used instead of 1-(6-methyl-2pyridyl)piperazine, to thereby obtain 148 mg of 2-[4-{4-(6-isopropoxy-2-pyridyl)-1-piperazinyl}butoxy]-5,6,7,8-tetrahydroquinoxaline (compound 630) (yield: 35%).

In substantially the same manner as in Example 1, the hydrochloride of the obtained 2-[4-{4-(6-isopropoxy-2-pyridyl)-1-piperazinyl}butoxy]-5,6,7,8-tetrahydroquinoxaline was obtained.

EXAMPLE 27

2-[4-{4-(4-Trifluoromethyl-2-pyridyl)-1-piperazinyl}-butoxy]-5,6,7,8-tetrahydroquinoxaline (compound 639)

Substantially the same procedure as in Example 13 was repeated, except that 277 mg (1.2 mmol) of 1-(4-trifluoromethyl-2-pyridyl)piperazine was used instead of 1-(6-methyl-2-pyridyl)piperazine, to thereby obtain 283 mg of 2-[4-{4-(4-trifluoromethyl-2-pyridyl)-1-piperazinyl}butoxy]-5,6,7, 8-tetrahydroquinoxaline (compound 639) (yield: 65%).

In substantially the same manner as in Example 1, the hydrochloride of the obtained 2-[4-{4-(4-trifluoromethyl-2-pyridyl)-1-piperazinyl}butoxy]-5,6,7,8-tetrahydroquinoxaline was obtained.

EXAMPLE 28

2-[4-{4-(6-Trifluoromethyl-2-pyridyl)-1-piperazinyl}-butoxy]-5,6,7,8-tetrahydroquinoxaline (compound 640)

Substantially the same procedure as in Example 13 was repeated, except that 277 mg (1.2 mmol) of 1-(6-trifluoromethyl-2-pyridyl)piperazine was used instead of 1-(6-methyl-2-pyridyl)piperazine, to thereby obtain 281 mg of 2-[4-{4-(6-trifluoromethyl-2-pyridyl)-1-piperazinyl}butoxy]-5,6,7,8-tetrahydroquinoxaline (compound 640) (yield: 65%).

In substantially the same manner as in Example 1, the hydrochloride of the obtained 2-[4-{4-(6-trifluoromethyl-2-pyridyl)-1-piperazinyl}butoxy]-5,6,7,8-tetrahydroquinoxaline was obtained.

EXAMPLE 29

2-[4-{4-(4-Methyl-2-pyrimidinyl)-1-piperazinyl}-butoxy]-5,6,7,8-tetrahydroquinoxaline (compound 504)

Substantially the same procedure as in Example 13 was repeated, except that 214 mg (1.2 mmol) of 1-(4-methyl-2-pyrimidinyl)piperazine was used instead of 1-(6-methyl-2-pyridyl)piperazine, to thereby obtain 174 mg of 2-[4-{4-(4-methyl-2-pyrimidinyl)-1-piperazinyl}butoxy]-5,6,7,8-tetrahydroquinoxaline (compound 504) (yield: 45%).

In substantially the same manner as in Example 1, the hydrochloride of the obtained 2-[4-{4-(4-methyl-2-pyrimidinyl)-1-piperazinyl}butoxy]-5,6,7,8-tetrahydroquinoxaline was obtained.

EXAMPLE 30

2-[4-{4-(4,6-Dimethoxy-2-pyrimidinyl)-1-piperazinyl}-butoxy]-5,6,7,8-tetrahydroquinoxaline (compound 549)

Substantially the same procedure as in Example 13 was repeated, except that 269 mg (1.2 mmol) of 1-(4,6-dimethoxy-2-pyrimidinyl)piperazine was used instead of 1-(6-methyl-2-pyridyl)piperazine, to thereby obtain 171 mg of 2-[4-{4-(4,6-dimethoxy-2-pyrimidinyl)-1-piperazinyl}butoxy]-5,6,7,8-tetrahydroquinoxaline (compound 549) (yield: 40%).

In substantially the same manner as in Example 1, the hydrochloride of the obtained 2-[4-{4-(4,6-dimethoxy-2-pyrimidinyl)-1-piperazinyl}butoxy]-5,6,7,8-tetrahydroquinoxaline was obtained.

EXAMPLE 31

2-[4-{4-(4-Methoxy-6-methyl-2-pyrimidinyl)-1-piperazinyl}butoxy]-5,6,7,8-tetrahydroquinoxaline (compound 562)

Substantially the same procedure as in Example 13 was repeated, except that 250 mg (1.2 mmol) of 1-(4-methoxy-6-methyl-2-pyrimidinyl)piperazine was used instead of 1-(6-methyl-2-pyridyl)piperazine, to thereby obtain 373 mg of 2-[4-{4-(4-methoxy-6-methyl-2-pyrimidinyl)-1-piperazinyl}butoxy]-5,6,7,8-tetrahydroquinoxaline (compound 562) (yield: 90%).

In substantially the same manner as in Example 1, the hydrochloride of the obtained 2-[4-{4-(4-methoxy-6-methyl-2-pyrimidinyl)-1-piperazinyl}butoxy]-5,6,7,8-tetrahydroquinoxaline was obtained.

EXAMPLE 32

2-[2-{4-(2-Pyridyl)-1-piperazinyl}ethoxy]-5,6,7,8-tetrahydroquinoxaline (compound 517)

291 mg (1.5 mmol) of 2-(2-hydroxyethoxy)-5,6,7,8-tetrahydroquinoxaline was dissolved in 15 ml of methylene chloride. To the resultant solution was added 0.25 ml (1.8 mmol) of triethylamine and then, 0.13 ml (1.65 mmol) of methanesulfonyl chloride was added dropwise thereto. The resultant mixture was stirred at room temperature for 2.5 hours to effect a reaction. To the resultant reaction mixture was added chloroform to obtain a mixture. The mixture was extracted with an aqueous potassium carbonate solution to thereby obtain an organic layer and an aqueous layer. The aqueous layer was subjected to extraction with chloroform to obtain an additional organic layer. The two organic layers were combined, dried over sodium sulfate, and subjected to filtration, followed by concentration, to thereby obtain 408 mg of 2-(2-methanesulfonyloxyethoxy)-5,6,7,8-tetrahydroquinoxaline. The thus obtained 2-(2-methanesulfonyloxyethoxy)-5,6,7,8-tetrahydroquinoxaline was dissolved in 10 ml of acetonitrile. To the resultant solution were added 0.31 g (2.25 mmol) of potassium carbonate and 294 mg (1.8 mmol) of 1-(2-pyridyl)piperazine, and the resultant mixture was heated under reflux for 24 hours. Then, the mixture was subjected to filtration to filter off insoluble substances, which were then washed with acetonitrile, to thereby obtain a filtrate. The solvent of the filtrate was distilled off in vacuo to thereby obtain a residue. The obtained residue was purified by silica gel column chromatography. That is, the residue was charged in a column of 20 g of silica gel (Art7734, manufactured and sold by E. Merck, Darmstadt) and eluted with chloroform-methanol (100:1), to thereby obtain 522 mg of 2-[2-{4-(2-pyridyl)-1-piperazinyl}ethoxy]-5,6,7,8-tetrahydroquinoxaline (compound 517) (yield: 100%).

In substantially the same manner as in Example 1, the hydrochloride of the obtained 2-[2-{4-(2-pyridyl)-1-piperazinyl}ethoxy]-5,6,7,8-tetrahydroquinoxaline was obtained.

EXAMPLE 33

2-[2-{4-(2-Pyrimidinyl)-1-piperazinyl}ethoxy]-5,6,7,8-tetrahydroquinoxaline (compound 521)

Substantially the same procedure as in Example 32 was repeated, except that 296 mg (1.8 mmol) of 1-(2-pyrimidiyl)piperazine was used instead of 1-(2-pyridyl)piperazine, to thereby obtain 407 mg of 2-[2-{4-(2-pyrimidinyl)-1-piperazinyl}ethoxy]-5,6,7,8-tetrahydroquinoxaline (compound 521) (yield: 80%).

In substantially the same manner as in Example 1, the hydrochloride of the obtained 2-[2-{4-(2-pyrimidinyl)-1-piperazinyl}ethoxy]-5,6,7,8-tetrahydroquinoxaline was obtained.

EXAMPLE 34

2-[3-{4-(2-Pyridyl)-1-piperazinyl}propoxy]-5,6,7,8-tetrahydroquinoxaline (compound 537)

227 mg (1 mmol) of 2-(3-chloropropoxy)-5,6,7,8-tetrahydroquinoxaline was dissolved in 10 ml of acetonitrile. To the resultant solution were added 208 mg (1.5 mmol) of potassium carbonate, 196 mg (1.2 mmol) of 1-(2-pyridyl)piperazine and 149 mg (1 mmol) of sodium iodide, and the resultant mixture was heated under reflux for 15 hours. Then, the mixture was subjected to filtration to filter off insoluble substances, which were then washed with acetonitrile, to thereby obtain a filtrate. The solvent of the filtrate was distilled off in vacuo to thereby obtain a residue. The obtained residue was purified by silica gel column chromatography. That is, the residue was charged in a column of 20 g of silica gel (Art7734, manufactured and sold by E. Merck, Darmstadt) and eluted with chloroform-methanol (100:1), to thereby obtain 279 mg of 2-[3-{4-(2-pyridyl)-1-piperazinyl}propoxy]-5,6,7,8-tetrahydroquinoxaline (yield: 79%).

In substantially the same manner as in Example 1, the hydrochloride of the obtained 2-[3-{4-(2-pyridyl)-1-piperazinyl}propoxy]-5,6,7,8-tetrahydroquinoxaline was obtained.

EXAMPLE 35

2-[3-{4-(2-pyrimidinyl)-1-piperazinyl}propoxy]-5,6,7,8-tetrahydroquinoxaline (compound 538).

Substantially the same procedure as in Example 34 was repeated, except that 197 mg (1.2 mmol) of 1-(2-pyrimidinyl)piperazine was used instead of 1-(2-pyridyl)piperazine, to thereby obtain 198 mg of 2-[3-{4-(2-pyrimidinyl)-1-piperazinyl}propoxy]-5,6,7,8-tetrahydroquinoxaline (compound 538) (yield: 56%).

In substantially the same manner as in Example 1, the hydrochloride of the obtained 2-[3-{4-(2-pyrimidinyl)-1-piperazinyl}propoxy]-5,6,7,8-tetrahydroquinoxaline was obtained.

EXAMPLE 36

2-[5-{4-(2-Pyridyl)-1-piperazinyl}pentoxy]-5,6,7,8-tetrahydroquinoxaline (compound 511)

255 mg (1 mmol) of 2-(5-chloropentoxy)-5,6,7,8-tetrahydroquinoxaline was dissolved in 10 ml of acetonitrile. To the resultant solution were added 208 mg (1.5 mmol) of potassium carbonate, 196 mg (1.2 mmol) of 1-(2-pyridyl)piperazine and 149 mg (1 mmol) of sodium iodide, and the resultant mixture was heated under reflux for 25 hours. Then, the mixture was subjected to filtration to filter off insoluble substances, which were then washed with acetonitrile, to thereby obtain a filtrate. The solvent of the filtrate was distilled off in vacuo to thereby obtain a residue. The obtained residue was purified by silica gel column chromatography. That is, the residue was charged in a column of 20 g of silica gel (Art7734, manufactured and sold by E. Merck, Darmstadt) and eluted with chloroform-methanol (100:1), to thereby obtain 160 mg of 2-[5-{4-(2-pyridyl)-1-piperazinyl}pentoxy]-5,6,7,8-tetrahydroquinoxaline (compound 511) (yield: 42%).

In substantially the same manner as in Example 1, the hydrochloride of the obtained 2-[5-{4-(2-pyridyl)-1-piperazinyl}pentoxy]-5,6,7,8-tetrahydroquinoxaline was obtained.

EXAMPLE 37

2-[5-{4-(2-pyrimidinyl)-1-piperazinyl}pentoxy]-5,6,7,8-tetrahydroquinoxaline (compound 512)

Substantially the same procedure as in Example 36 was repeated, except that 197 mg (1.2 mmol) of 1-(2-pyrimidiyl)piperazine was used instead of 1-(2-pyridyl)piperazine, to thereby obtain 212 mg of 2-[5-{4-(2-pyrimidinyl)-1-piperazinyl}pentoxy]-5,6,7,8-tetrahydroquinoxaline (compound 512) (yield: 56%).

In substantially the same manner as in Example 1, the hydrochloride of the obtained 2-[5-{4-(2-pyrimidinyl)-1-piperazinyl}pentoxy]-5,6,7,8-tetrahydroquinoxaline was obtained.

TABLE 9

| Reference Example No. | $^1$H-NMR(CDCl$_3$, TMS) δ: (J:Hz) | MASS (FAB) |
|---|---|---|
| 1 | 1.7–1.9(4H, m), 2.6–2.8(4H, m), 8.04(1H, s) | 151 (MH$^+$) |
| 2 | 1.26(3H, t, J=7.1), 1.8–2.0(4H, m), 2.0–2.2(2H, m), 2.49(2H, t, J=7.4), 2.7–3.0(4H, m), 4.14(2H, q, J=7.1), 4.31(2H, t, J=6.3), 7.95(1H, s) | 265 (MH$^+$) 151 |
| 3 | 1.26(3H, t, J=7.1), 1.7–2.0(4H, m), 2.0–2.2(2H, m), 2.39(3H, s), 2.49(2H, t, J=7.4), 2.6–2.9(4H, m), 4.15(2H, q, J=7.1), 4.32(2H, t, J=6.3) | 279 (MH$^+$) 151 |
| 4 | 0.97(3H, t, J=7.3), 1.26(3H, t, J=7.1), 1.55–1.75(2H, m), 1.7–2.0(4H, m), 2.0–2.2(2H, m), 2.46(2H, t, J=7.4), 2.6–2.9(6H, m), 4.15(2H, q, J=7.1), 4.31(2H, t, J=6.3) | 307 (MH$^+$) 151 |
| 5 | 1.24(6H, d, J=6.9), 1.26(3H, t, J=7.1), 1.7–2.0(4H, m), 2.0–2.2(2H, m), 2.49(2H, t, J=7.4), 2.6–2.9(4H, m), 3.2–3.4(1H, m), 4.15(2H, q, J=7.1), 4.31(2H, t, J=6.3) | 307 (MH$^+$) 151 |
| 6 | 0.89(3H, t, J=7.0), 1.26(3H, t, J=7.1), 1.3–1.4(4H, m), 1.5–1.7(2H, m), 1.8–2.0(4H, m), 2.0–2.2(2H, m), 2.46(2H, t, J=7.4), 2.6–2.9(6H, m), 4.15(2H, q, J=7.1), 4.31(2H, t, J=6.3) | 335 (MH$^+$) 151 |
| 7 | 1.6–2.0(8H, m), 2.7–2.9(4H, m), 3.6–3.8(2H, m), 4.32(2H, t, J=6.3), 7.96(1H, s) | 223 (MH$^+$) 151 |
| 8 | 1.6–1.9(8H, m), 2.40(3H, s), 2.7–2.9(4H, m), 3.6–3.8(2H, m), 4.33(2H, t, J=6.3) | 237 (MH$^+$) 151 |
| 9 | 0.97(3H, t, J=7.3), 1.6–2.0(10H, m), 2.6–2.9(6H, m), 3.65–3.85(2H, m), 4.32(2H, t, J=6.3) | 265 (MH$^+$) 151 |
| 10 | 1.23(6H, d, J=6.9), 1.6–2.0(8H, m), 2.6–2.9(4H, m), 3.2–3.4(1H, m), 3.6–3.8(2H, m), 4.32(2H, t, J=6.3) | 265 (MH$^+$) 151 |
| 11 | 0.89(3H, t, J=7.0), 1.2–1.4(4H, m), 1.5–1.9(10H, m), 2.4–2.9(6H, m), 3.65–3.85(2H, m), 4.32(2H, t, J=6.3) | 293 (MH$^+$) 151 |
| 12 | 1.8–2.0(8H, m), 2.7–2.9(4H, m), 3.02(3H, s), 4.2–4.4(4H, m), 7.95(1H, s) | 301 (MH$^+$) 151 |
| 13 | 1.8–2.0(8H, m), 2.40(3H, s), 2.7–2.9(4H, m), 3.02(3H, s), 4.3–4.4(4H, m) | 315 (MH$^+$) |
| 14 | 0.97(3H, t, J=7.3), 1.6–1.7(2H, m), 1.8–2.0(8H, m), 2.6–2.8(6H, m), 3.02(3H, s), 4.3–4.4(4H, m) | 343 (MH$^+$) |
| 15 | 1.24(6H, d, J=6.9), 1.8–2.0(8H, m), 2.7–2.8(4H, m), 3.02(3H, s), 3.15–3.35(1H, m), 4.3–4.4(4H, m) | 343 (MH$^+$) |
| 16 | 0.89(3H, t, J=6.9), 1.3–1.4(4H, m), 1.6–1.7(2H, m), 1.8–2.0(8H, m), 2.6–2.9(6H, m), 3.02(3H, s), 4.3–4.4(4H, m) | 371 (MH$^+$) |
| 17 | 1.8–2.0(8H, m), 2.7–2.9(4H, m), 3.62(2H, t, J=6.3), 4.31(2H, t, J=5.9), | 243, 241 |

TABLE 9-continued

| Reference Example No. | ¹H-NMR(CDCl₃, TMS) δ: (J:Hz) | MASS (FAB) |
|---|---|---|
| | 7.95(1H, s) | (MH⁺) |
| 18 | 1.24(6H, d, J=6.9), 1.8~2.0(8H, m), 2.7~2.9(4H, m), 3.2~3.35(1H, m), 3.63(2H, t, J=6.3), 4.31(2H, t, J=5.9) | 285, 283 (MH⁺) |
| 19 | 1.34(3H, t, J=7.3), 1.8~2.0(4H, m), 2.8~3.0(4H, m), 4.30(2H, q, J=7.3), 4.92(2H, s), 8.16(1H, s) | 237 (MH⁺) |
| 20 | 1.8~2.0(4H, m), 2.7~2.9(4H, m), 3.22(1H, t, J=5.8), 3.9~4.1(2H, m), 4.4~4.5(2H, m), 8.04(1H, s) | 195 (MH⁺) |
| 21 | 1.8~2.0(4H, m), 2.15~2.3(2H, m), 2.75~2.95(4H, m), 3.72(2H, t, J=6.3), 4.43(2H, t, J=5.9), 7.97(1H, s) | 229, 227 (MH⁺) |
| 22 | 1.55~1.7(2H, m), 1.75~1.95(8H, m), 2.75~2.95(4H, m), 3.56(2H, t, J=6.6), 4.28(2H, t, J=6.3), 7.95(1H, s) | 257, 255 (MH⁺) |

TABLE 10

| Compound No. | ¹H-NMR(CDCl₃, TMS) δ: (J:Hz) | MASS (FAB) |
|---|---|---|
| 300 | 1.6~2.0(8H, m), 2.45(2H, t, J=7.4), 2.5~2.7(4H, m), 2.7~2.9(4H, m), 3.5~3.7(4H, m), 4.30(2H, t, J=6.3), 6.5~6.7(2H, m), 7.4~7.6(1H, m), 7.95(1H, s), 8.1~8.3(1H, m) | 368 (MH⁺) 216 |
| 301 | 1.6~2.0(8H, m), 2.4~2.7(6H, m), 2.7~3.0(4H, m), 3.7~3.9(4H, m), 4.30(2H, t, J=6.3), 6.47(1H, t, J=4.6), 7.95(1H, s), 8.30(2H, d, J=4.6) | 369 (MH⁺) 217 |
| 409 | 1.65~1.8(4H, m), 1.8~1.9(4H, m), 2.41(3H, s), 2.47(2H, t, J=7.4), 2.57(4H, t, J=5.0), 2.7~2.9(4H, m), 3.56(4H, t, J=5.0), 4.31(2H, t, J=6.3), 6.6~6.7(2H, m), 7.4~7.55(1H, m), 8.19(1H, dd, J=1.5, 4.6) | 382 (MH⁺) 216 |
| 410 | 1.65~1.9(8H, m), 2.40(3H, s), 2.46(2H, t, J=7.4), 2.51(4H, t, J=5.0), 2.7~2.9(4H, m), 3.84(4H, t, J=5.0), 4.30(2H, t, J=6.3), 6.48(1H, t, J=4.6), 8.31(2H, d, J=4.6) | 383 (MH⁺) 219 |
| 423 | 0.97(3H, t, J=7.3), 1.6~1.75(6H, m), 1.75~1.9(4H, m), 2.47(2H, t, J=7.4), 2.57(4H, t, J=5.1), 2.72(2H, t, J=7.8), 2.7~2.9(4H, m), 3.55(4H, t, J=5.1), 4.30(2H, t, J=6.1), 6.6~6.7(2H, m), 7.45~7.5(1H, m), 8.19(1H, dd, J=1.8, 4.6) | 410 (MH⁺) 216 |
| 414 | 0.97(3H, t, J=7.4), 1.6~1.8(6H, m), 1.8~1.9(4H, m), 2.46(2H, t, J=7.4), 2.51(4H, t, J=5.0), 2.72(2H, t, J=7.8), 2.7~2.9(4H, m), 3.84(4H, t, J=5.0), 4.30(2H, t, J=6.1), 6.48(1H, t, J=4.6), 8.30(2H, d, J=4.6) | 411 (MH⁺) 219 |
| 431 | 1.25(6H, d, J=6.9), 1.6~1.9(8H, m), 2.47(2H, t, J=7.3), 2.57(4H, t, J=5.0), 2.7~2.9(4H, m), 3.2~3.4(1H, m), 3.55(4H, t, J=5.0), 4.30(2H, t, J=6.1), 6.5~6.7(2H, m), 7.4~7.5(1H, m), 8.19(1H, dd, J=2.0, 5.0) | 410 (MH⁺) 218 |
| 432 | 1.24(6H, d, J=6.9), 1.6~1.9(8H, m), 2.46(2H, t, J=7.6), 2.51(4H, t, J=5.0), 2.7~2.9(4H, m), 3.2~3.4(1H, m), 3.84(4H, t, J=5.0), 4.30(2H, t, J=6.1), 6.48(1H, t, J=4.9), 8.30(2H, d, J=4.9) | 411 (MH⁺) 219 |
| 425 | 0.90(3H, t, J=6.9), 1.3~1.4(4H, m), 1.6~1.9(10H, m), 2.46(2H, t, J=7.4), 2.57(4H, t, J=5.1), 2.7~2.9(6H, m), 3.55(4H, t, J=5.1), 4.30(2H, t, J=6.1), 6.6~6.7(2H, m), 7.4~7.5(1H, m), 8.19(1H, dd, J=1.5, 4.5) | 438 (MH⁺) 218 |
| 428 | 0.89(3H, t, J=7.1), 1.3~1.4(4H, m), 1.6~1.9(10H, m), 2.45(2H, t, J=7.4), 2.51(4H, t, J=5.1), 2.7~2.9(6H, m), | 439 (MH⁺) 219 |

TABLE 10-continued

| Compound No. | ¹H-NMR(CDCl₃, TMS) δ: (J:Hz) | MASS (FAB) |
|---|---|---|
| | 3.83(4H, t, J=5.0), 4.30(2H, t, J=6.1), 6.48(1H, t, J=4.6), 8.30(2H, d, J=4.6) | |
| 517 | 1.75~1.9(4H, m), 2.6~2.85(10H, m), 3.53(4H, t, J=5.0), 4.13(2H, t, J=6.8), 6.6~6.7(2H, m), 7.4~7.5(1H, m), 8.03(1H, s), 8.15~8.25(1H, m) | 340 (MH⁺) |
| 521 | 1.7~1.9(4H, m), 2.60(4H, t, J=5.0), 2.65~2.85(6H, m), 3.81(4H, t, J=5.0), 4.13(2H, t, J=6.8), 6.49(1H, t, J=4.6), 8.03(1H, s), 8.31(2H, d, J=4.6) | 341 (MH⁺) |
| 537 | 1.75~2.0(6H, m), 2.47(2H, t, J=6.8), 2.56(4H, t, J=5.1)2.6~2.8(4H, m), 3.53(4H, t, J=5.1), 4.05(2H, t, J=7.6), 6.6~6.7(2H, m), 7.4~7.5(1H, m), 8.01(1H, s), 8.15~8.2(1H, m) | 354 (MH⁺) |
| 538 | 1.75~2.0(6H, m), 2.47(2H, t, J=6.9), 2.50(4H, t, J=5.0), 2.6~2.8(4H, m), 3.81(4H, t, J=5.0), 4.06(2H, t, J=7.6), 6.49(1H, t, J=4.6), 8.02(1H, s), 8.31(2H, d, J=4.6) | 355 (MH⁺) |
| 511 | 1.5~1.7(4H, m), 1.75~2.0(6H, m), 2.42(2H, t, J=7.4), 2.56(4H, t, J=5.0), 2.7~2.9(4H, m), 3.55(4H, t, J=5.0), 4.27(2H, t, J=6.6), 6.6~6.7(2H, m), 7.45~7.5(1H, m), 7.96(1H, s), 8.19(1H, d, J=4.6) | 382 (MH⁺) |
| 512 | 1.55~1.7(4H, m), 1.75~1.95(6H, m), 2.40(4H, t, J=7.6), 2.50(4H, t, J=5.1), 2.7~2.9(4H, m), 3.83(4H, t, J=5.1), 4.27(2H, t, J=6.6), 6.47(1H, t, J=4.6), 7.95(1H, s), 8.30(2H, d, J=4.6) | 383 (MH⁺) |
| 501 | 1.65~1.8(4H, m), 1.8~1.9(4H, m), 2.39(3H, s), 2.45(2H, t, J=7.4), 2.56(4H, t, J=5.0), 2.7~2.9(4H, m), 3.54(4H, t, J=5.0), 4.30(2H, t, J=6.3), 6.43(1H, d, J=8.3), 6.48(1H, d, J=7.3), 7.3~7.4(1H, m), 7.95(1H, s) | 382 (MH⁺) |
| 502 | 1.65~1.8(4H, m), 1.8~1.9(4H, m), 2.48(2H, t, J=7.4), 2.63(4H, t, J=4.8), 2.7~2.9(4H, m), 3.40(4H, t, J=4.8), 4.30(2H, t, J=6.3), 6.82(1H, dd, J=5.0, 7.6), 7.57(1H, dd, J=1.7, 7.6), 7.95(1H, s), 8.18(1H, dd, J=1.7, 5.0) | 402 (MH⁺) |
| 557 | 1.6~1.9(8H, m), 2.47(2H, t, J=7.4), 2.63(4H, br.s), 2.7~2.9(4H, m), 3.45(4H, br.s), 3.85(3H, s), 4.30(2H, t, J=6.3), 6.82(1H, dd, J=5.0, 7.9), 7.03(1H, d, J=7.9), 7.87(1H, d, J=5.0), 7.95(1H, s) | 398 (MH⁺) |
| 514 | 1.65~1.8(4H, m), 1.8~1.9(4H, m), 2.47(2H, t, J=7.3), 2.60(4H, t, J=5.0), 2.7~2.9(4H, m), 3.75(4H, t, J=5.0), 4.30(2H, t, J=6.3,), 6.73(1H, dd, J=4.6, 7.6), 7.76(1H, dd, J=2.0, 7.6), 7.96(1H, s), 8.33(1H, dd, J=2.0, 4.6) | 393 (MH⁺) |
| 598 | 1.6~2.0(8H, m), 2.21(3H, s), 2.41(3H, s), 2.47(2H, t, J=7.3), 2.5~2.7(3H, m), 2.7~2.9(4H, m), 3.1~3.25(3H, m), 3.55~3.65(1H, m), 4.2~4.4(3H, m), 6.67(1H, d, J=7.6), 7.25(1H, d, J=7.6), 7.96(1H, s) | 396 (MH⁺) |
| 500 | 1.6~1.8(4H, m), 1.8~1.9(4H, m), 2.44(2H, t, J=7.4), 2.53(4H, t, J=5.3), 2.7~2.9(4H, m), 3.55(4H, t, J=5.3), 4.30(2H, t, J=6.3), 6.48(1H, d, J=8.2), 6.59(1H, d, J=7.6), 7.35~7.45(1H, m), 7.95(1H, s) | 402 (MH⁺) |
| 524 | 1.37(3H, t, J=6.9), 1.65~1.8(4H, m), 1.8~1.9(4H, m), 2.45(2H, t, J=7.4), 2.54(4H, t, J=5.1), 2.7~2.9(4H, m), 3.52(4H, t, J=5.1), 4.29(2H, q, J=6.9), 4.30(2H, t, J=6.4), 6.05(1H, d, J=7.9), 6.14(1H, d, J=7.9), 7.39(1H, t, J=7.9), 7.96(1H, s) | 412 (MH⁺) |
| 526 | 1.65~1.85(4H, m), 1.85~1.9(4H, m), 2.47(2H, t, J=7.3), 2.62(4H, t, J=5.0), | 411 (MH⁺) |

TABLE 10-continued

| Compound No. | $^1$H-NMR(CDCl$_3$, TMS) δ: (J:Hz) | MASS (FAB) |
|---|---|---|
| | 2.7~2.9(4H, m), 3.26(4H, t, J=5.0), 4.30(2H, t, J=6.3), 5.91(1H, br.s), 7.08(1H, dd, J=4.6, 7.6), 7.95(1H, s), 8.29(1H, dd, J=2.0, 7.6), 8.40(1H, dd, J=2.0, 4.6), 8.47(1H, br.s) | |
| 539 | 1.6~1.85(4H, m), 1.85~1.9(4H, m), 2.45(2H, t, J=7.4), 2.56(4H, t, J=5.0), 2.7~2.9(4H, m), 3.53(4H, t, J=5.0), 3.87(3H, s), 4.30(2H, t, J=6.4), 6.07(1H, d, J=7.9), 6.15(1H, d, J=7.9), 7.40(1H, t, J=7.9), 7.96(1H, s) | 398 (MH$^+$) |
| 561 | 1.6~1.9(8H, m), 2.39(3H, s), 2.40(3H, s), 2.46(2H, t, J=7.3), 2.59(4H, t, J=5.0), 2.7~2.9(4H, m), 3.68(4H, t, J=5.0), 4.30(2H, t, J=6.3), 6.52(1H, s), 7.96(1H, s) | 421 (MH$^+$) |
| 569 | 1.65~1.85(4H, m), 1.85~1.9(4H, m), 2.21(3H, s), 2.36(3H, s), 2.45(2H, t, J=7.4), 2.55(4H, t, J=5.1), 2.7~2.9(4H, m), 3.52(4H, t, J=5.1), 4.30(2H, t, J=6.3), 6.26(1H, s), 6.35(1H, s), 7.95(1H, s) | 396 (MH$^+$) |
| 621 | 1.65~1.85(4H, m), 1.85~1.9(4H, m), 2.47(2H, t, J=7.4), 2.59(4H, t, J=4.8), 2.7~2.9(4H, m), 3.34(4H, t, J=4.8), 4.30(2H, t, J=6.3), 6.95(1H, dd, J=4.6, 7.9), 7.84(1H, dd, J=1.8, 7.9), 7.95(1H, s), 8.40~8.42(1H, m) | 436 (MH$^+$) |
| 629 | 1.00(3H, t, J=7.4), 1.65~1.95(10H, m), 2.45(2H, t, J=7.4), 2.55(4H, t, J=5.1), 2.7~2.9(4H, m), 3.51(4H, t, J=5.1), 4.18(2H, t, J=6.8), 4.30(2H, t, J=6.3), 6.06(1H, d, J=7.9), 6.13(1H, d, J=7.9), 7.38(1H, t, J=7.9), 7.95(1H, s) | 426 (MH$^+$) |
| 630 | 1.33(6H, d, J=6.3), 1.65~1.95(8H, m), 2.45(2H, t, J=7.4), 2.55(4H, t, J=5.1), 2.7~2.9(4H, m), 3.51(4H, t, J=5.1), 4.30(2H, t, J=6.4), 5.15~5.25(1H, m), 6.02(1H, d, J=7.9), 6.12(1H, d, J=7.9), 7.37(1H, t, J=7.9), 7.95(1H, s) | 426 (MH$^+$) |
| 639 | 1.65~1.95(8H, m), 2.46(2H, t, J=7.4), 2.56(4H, t, J=5.1), 2.7~2.9(4H, m), 3.61(4H, t, J=5.1), 4.30(2H, t, J=6.3), 6.77(1H, d, J=4.9), 6.78(1H, s), 7.96(1H, s), 8.29(1H, d, J=4.9) | 436 (MH$^+$) |
| 640 | 1.7~1.95(8H, m), 2.45(2H, t, J=7.4), 2.55(4H, t, J=5.1), 2.7~2.9(4H, m), 3.61(4H, t, J=5.1), 4.30(2H, t, J=6.3), 6.76(1H, d, J=7.9), 6.93(1H, d, J=7.9), 7.56(1H, t, J=7.9), 7.96(1H, s) | 436 (MH$^+$) |
| 481 | 1.6~1.9(8H, m), 2.28(6H, s), 2.4~2.6(6H, m), 2.8~2.9(4H, m), 3.84(4H, t, J=5.0), 4.30(2H, t, J=6.3), 6.25(1H, s), 7.96(1H, s) | 397 (MH$^+$) |
| 504 | 1.65~1.8(4H, m), 1.8~1.9(4H, m), 2.33(3H, s), 2.44(2H, t, J=7.4), 2.50(4H, t, J=5.0), 2.7~2.9(4H, m), 3.83(4H, t, J=5.0), 4.30(2H, t, J=6.3), 6.36(1H, d, J=5.0), 7.95(1H, s), 8.16(1H, d, J=5.0) | 383 (MH$^+$) |
| 549 | 1.65~1.85(4H, m), 1.85~1.9(4H, m), 2.44(2H, t, J=7.1), 2.48(4H, t, J=5.0), 2.7~2.9(4H, m), 3.81(4H, t, J=5.0), 3.85(6H, s), 4.30(2H, t, J=6.3), 5.36(1H, s), 7.95(1H, s) | 429 (MH$^+$) |
| 562 | 1.65~1.85(4H, m), 1.85~1.9(4H, m), 2.25(3H, s), 2.44(2H, t, J=7.9), 2.49(4H, t, J=5.3), 2.7~2.9(4H, m), 3.82(4H, t, J=5.3), 3.86(3H, s), 4.30(2H, t, J=6.3), 5.84(1H, s), 7.95(1H, s) | 413 (MH$^+$) |

We claim:

1. A compound represented by formula (1) or a non-toxic salt thereof

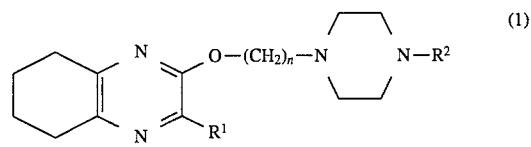

wherein $R^1$ represents hydrogen atom or a lower alkyl group; $R^2$ represents a pyridyl group which is unsubstituted or substituted with 1 to 3 substituents each independently selected from the group consisting of a halogen atom, a lower alkyl group, a tri-fluoromethyl group, a lower alkoxy group, a carbamoyl group and a cyano group, or a pyrimidinyl group which is unsubstituted or substituted with 1 to 2 substituents each independently selected from the group consisting of a lower alkyl group and a lower alkoxy group; and n is an integer of from 2 to 5.

2. A method for producing a compound represented by formula (1) or a non-toxic salt thereof,

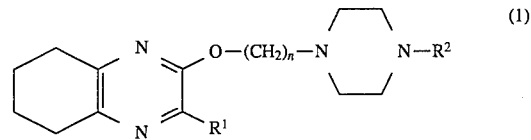

wherein $R^1$ represents a hydrogen atom or a lower alkyl group; $R^2$ represents a pyridyl group which is unsubstituted or substituted with 1 to 3 substituents each independently selected from the group consisting of a halogen atom, a lower alkyl group, a tri-fluromethyl group, a lower alkoxy group, a carbamoyl group and a cyano group, or a pyrimidinyl group which is unsubstituted or substituted with 1 to 2 substituents each independently selected from the group consisting of a lower alkyl group and a lower alkoxy group; and n is an integer of from 2 to 5, which comprises reacting, in an inert solvent, a compound represented by formula (2):

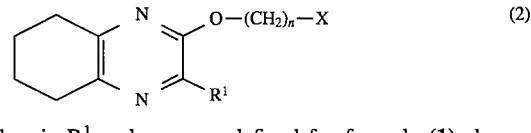

wherein $R^1$ and n are as defined for formula (1) above; and X represents a reactive leaving group, with a compound represented by formula (3):

wherein $R^2$ is as defined for formula (1) above.

3. A pharmaceutical composition for treating a serotonergic neuron-related disease, which comprises, as an active ingredient, a compound represented by formula (1) or a non-toxic salt thereof,

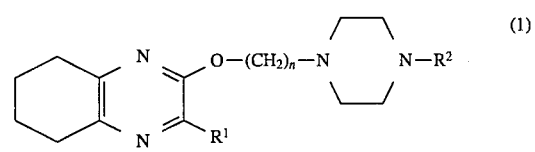

wherein $R^1$ represents a hydrogen atom or a lower alkyl group; $R^2$ represents a pyridyl group which is unsubstituted or substituted with 1 to 3 substituents each independently selected from the group consisting of a halogen atom, a lower alkyl group, a tri-fluoromethyl group, a lower alkoxy group, a carbamoyl group and a cyano group, or a pyrimidinyl group which is unsubstituted or substituted with 1 to 2 substituents each independently selected from the group consisting of a lower alkyl group and a lower alkoxy group; and n is an integer of from 2 to 5.

* * * * *